United States Patent
Hibner et al.

[11] Patent Number: 6,086,544
[45] Date of Patent: Jul. 11, 2000

[54] CONTROL APPARATUS FOR AN AUTOMATED SURGICAL BIOPSY DEVICE

[75] Inventors: John A. Hibner, Mason, Ohio; Chris K. Quatrochi, Homewood; Randy M. Raczek, Schaumburg, both of Ill.; Mark A. Burdorff, Loveland; Anthony T. Nguyen, Cincinnati, both of Ohio

[73] Assignee: Ethicon Endo-Surgery, Inc., Cincinnati, Ohio

[21] Appl. No.: 09/282,142

[22] Filed: Mar. 31, 1999

[51] Int. Cl.[7] .................................. A61B 10/00
[52] U.S. Cl. ................ 600/568; 600/564; 606/170
[58] Field of Search ............... 600/562, 564, 600/566, 567, 568; 604/22; 606/167, 168, 170, 171

[56] References Cited

U.S. PATENT DOCUMENTS

| | | | |
|---|---|---|---|
| Re. 33,258 | 7/1990 | Onik et al. | 604/22 |
| Re. 34,056 | 9/1992 | Lindgren et al. | 128/754 |
| Re. 34,556 | 3/1994 | Sjostrom et al. | 606/170 |
| 3,945,375 | 3/1976 | Banko | 128/6 |
| 3,996,935 | 12/1976 | Banko | 128/276 |
| 4,210,146 | 7/1980 | Banko | 128/305 |
| 4,250,892 | 2/1981 | Dolhay et al. | 128/758 |
| 4,320,761 | 3/1982 | Haddad | 128/305 |
| 4,699,154 | 10/1987 | Lindgren | 128/754 |
| 4,705,038 | 11/1987 | Sjostrom et al. | 128/305 |
| 4,802,487 | 2/1989 | Martin et al. | 128/662.06 |
| 4,832,685 | 5/1989 | Haines | 604/30 |
| 4,935,005 | 6/1990 | Haines | 604/30 |
| 4,940,061 | 7/1990 | Terwilliger et al. | 128/754 |
| 4,944,308 | 7/1990 | Akerfeldt | 128/751 |
| 4,995,877 | 2/1991 | Ams et al. | 606/180 |
| 5,027,827 | 7/1991 | Cody et al. | 128/753 |
| 5,112,299 | 5/1992 | Pascaloff | 604/22 |
| 5,133,661 | 7/1992 | Euvrard | 433/120 |
| 5,192,292 | 3/1993 | Cezana et al. | 606/170 |
| 5,217,478 | 6/1993 | Rexroth | 606/180 |
| 5,249,583 | 10/1993 | Mallaby | 128/754 |
| 5,275,609 | 1/1994 | Pingleton et al. | 606/170 |
| 5,320,635 | 6/1994 | Smith | 606/180 |
| 5,403,276 | 4/1995 | Schecter et al. | 604/22 |

(List continued on next page.)

FOREIGN PATENT DOCUMENTS

| | | | |
|---|---|---|---|
| WO 95/27443 | 10/1995 | WIPO | 606/159 |
| WO 98/06338 | 2/1998 | WIPO . | |
| WO 98/08446 | 3/1998 | WIPO | 604/22 |
| WO 98/09561 | 3/1998 | WIPO . | |
| WO 99/15079 | 4/1999 | WIPO . | |

*Primary Examiner*—Cary O'Connor
*Assistant Examiner*—Charles Marmor, II
*Attorney, Agent, or Firm*—Bernard E. Shay

[57] ABSTRACT

The present invention is a control apparatus for removing at least one tissue sample from a surgical patient using a surgical biopsy device. The biopsy device comprises an elongated piercer having a piercer lumen extending therethrough, and a cutter rotatably and axially positionable relative to the piercer. The piercer has a port for receiving and transferring the tissue sample into the piercer lumen. The biopsy device further comprises a rotation motor for rotating the cutter and a translation motor for translating the cutter in the axial direction. In one embodiment of the present invention, the control apparatus comprises a computing device for the coordinated control of the rotation and translation motors. The control apparatus further comprises a first sensor operationally connected to the rotation motor for supplying a rotation signal to the computing device for measuring the rotational speed of the cutter. The control apparatus further comprises a second sensor operationally connected to the translation motor for supplying a translation signal to the computing device for measuring the translational position and translational speed of the cutter. The control apparatus further comprises a first driver for driving the translation motor in response to a translation command from the computing device, and a second driver for driving the rotation motor in response to a rotation command from the computing device. The control apparatus automatically modifies the rotational speed and the translational speed of the cutter in response to the translational position and rotational resistance acting on the cutter.

7 Claims, 22 Drawing Sheets

U.S. PATENT DOCUMENTS

| | | | |
|---|---|---|---|
| 5,409,013 | 4/1995 | Clement | 128/753 |
| 5,429,138 | 7/1995 | Jamshidi | 128/753 |
| 5,437,630 | 8/1995 | Daniel et al. | 604/22 |
| 5,455,766 | 10/1995 | Scheller et al. | 364/413.01 |
| 5,492,130 | 2/1996 | Chiou | 128/753 |
| 5,505,210 | 4/1996 | Clement | 128/753 |
| 5,526,821 | 6/1996 | Jamshidi | 128/753 |
| 5,526,822 | 6/1996 | Burbank et al. | 128/754 |
| 5,529,532 | 6/1996 | Desrosiers | 451/344 |
| 5,543,695 | 8/1996 | Culp et al. | 318/432 |
| 5,602,449 | 2/1997 | Krause et al. | 318/254 |
| 5,603,724 | 2/1997 | O'Connor | 606/207 |
| 5,618,293 | 4/1997 | Sample et al. | 606/170 |
| 5,620,447 | 4/1997 | Smith et al. | 606/79 |
| 5,643,304 | 7/1997 | Schecter et al. | 606/171 |
| 5,649,547 | 7/1997 | Ritchart et al. | 128/754 |
| 5,669,876 | 9/1997 | Schechter et al. | 604/22 |
| 5,685,838 | 11/1997 | Peters et al. | 604/22 |
| 5,685,840 | 11/1997 | Schechter et al. | 604/22 |
| 5,689,159 | 11/1997 | Culp et al. | 318/254 |
| 5,690,660 | 11/1997 | Kauker et al. | 606/180 |
| 5,697,898 | 12/1997 | Devine | 604/22 |
| 5,728,004 | 3/1998 | Shan | 600/145 |
| 5,769,086 | 6/1998 | Ritchart et al. | 128/753 |
| 5,772,654 | 6/1998 | Leyva | 606/1 |
| 5,775,333 | 7/1998 | Burbank et al. | 128/754 |
| 5,779,647 | 7/1998 | Chau et al. | 600/564 |
| 5,795,308 | 8/1998 | Russin | 600/567 |
| 5,804,936 | 9/1998 | Brodsky et al. | 318/254 |
| 5,830,219 | 11/1998 | Bird et al. | 606/130 |
| 5,849,023 | 12/1998 | Mericle | 606/180 |
| 5,928,164 | 7/1999 | Burbank et al. | 600/567 |
| 5,944,673 | 8/1999 | Gregoire et al. | 600/564 |
| 5,980,469 | 11/1999 | Burbank et al. | 600/567 |
| 6,007,497 | 12/1999 | Huitema | 600/567 |

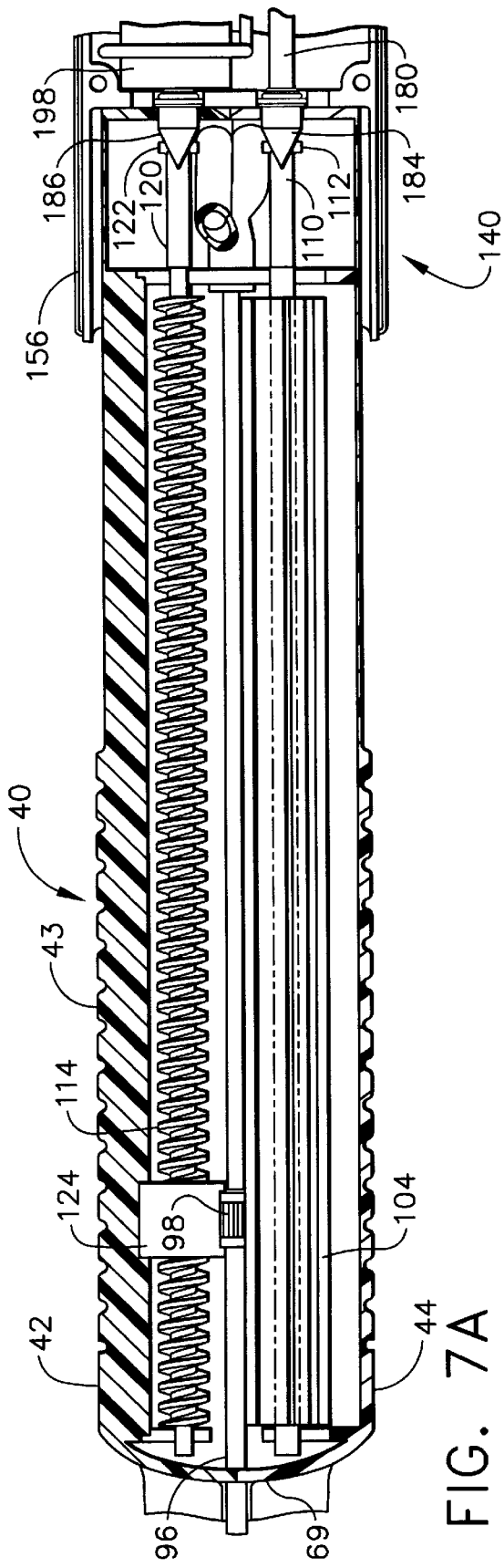
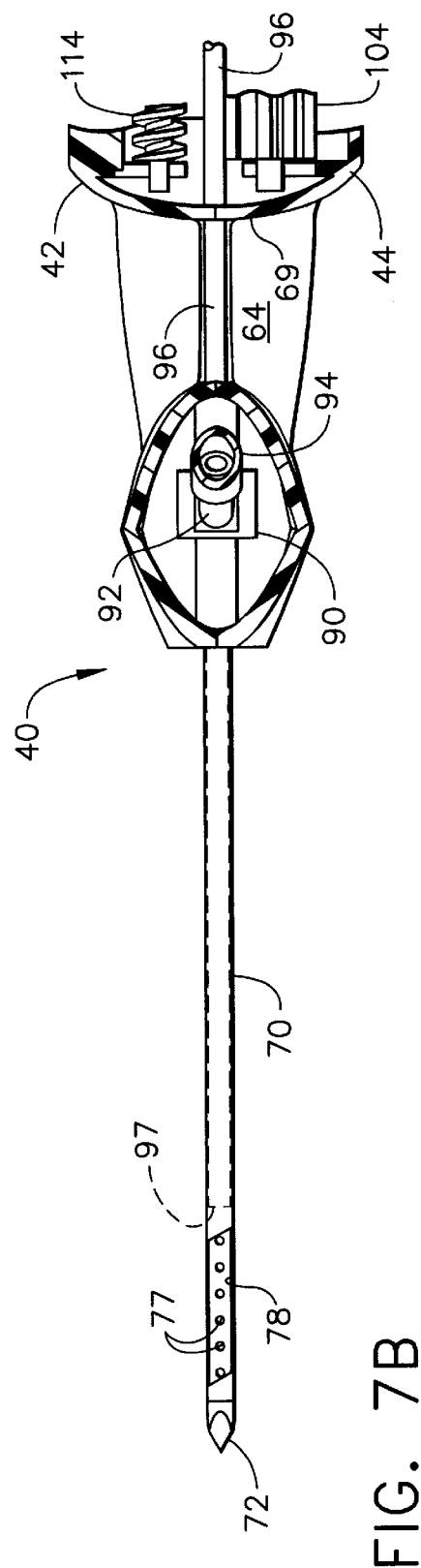
FIG. 7A
FIG. 7B

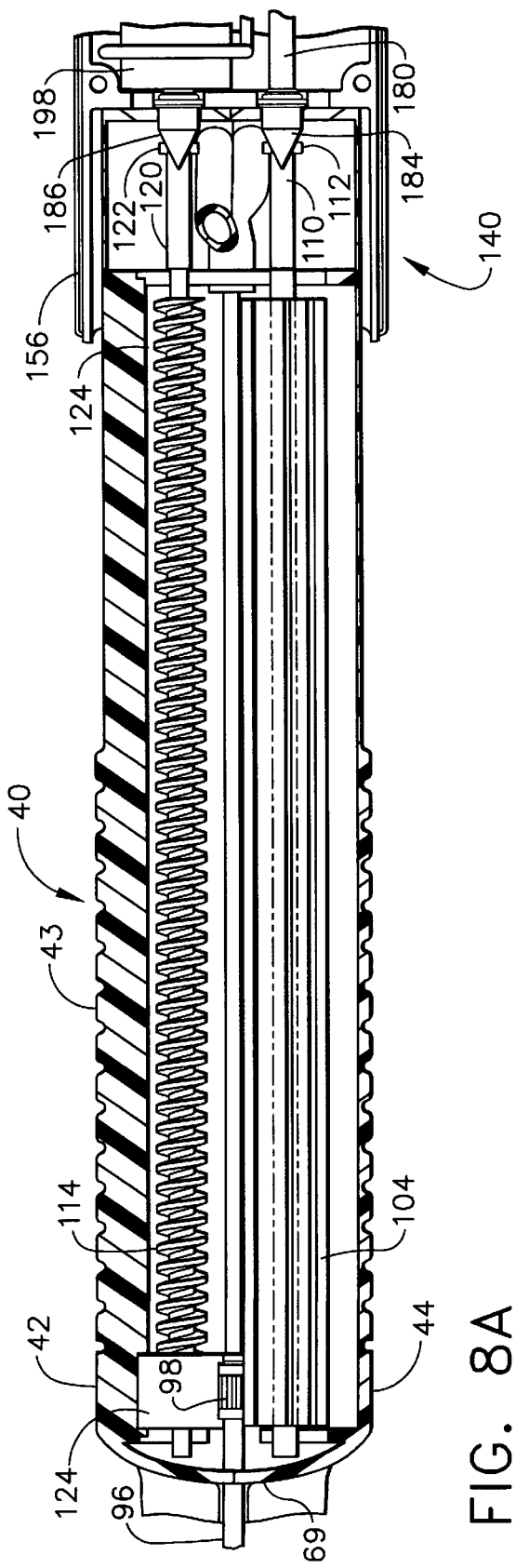
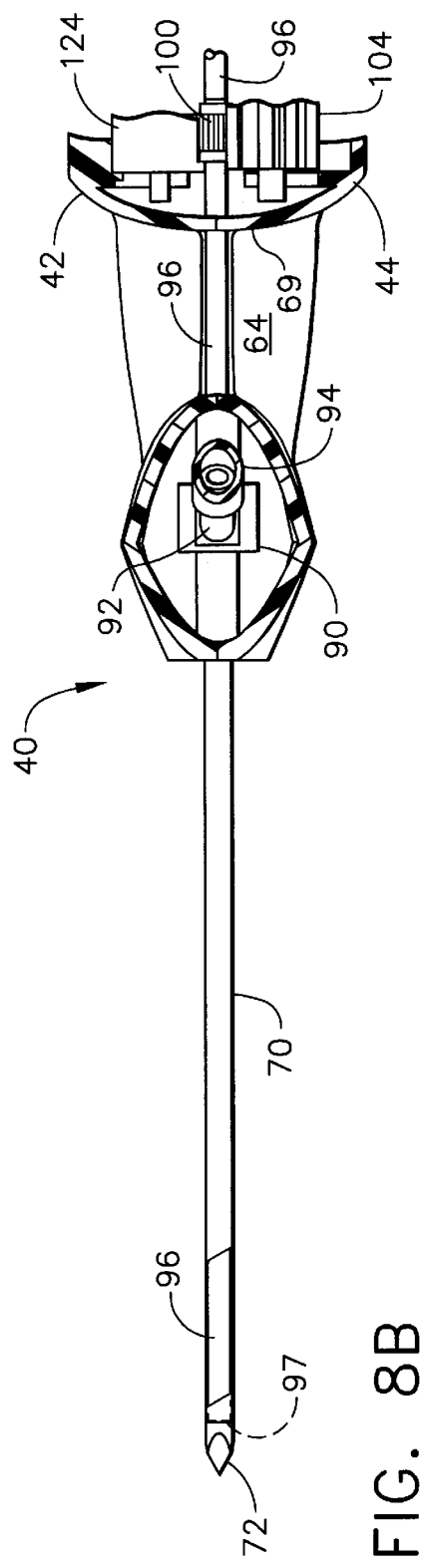
FIG. 8A
FIG. 8B

CONTROL APPARATUS FOR AN AUTOMATED SURGICAL BIOPSY DEVICE

This application is related to the following co-pending U.S. patent applications: Ser. No. 08/825,899 filed on Apr. 2, 1997; Ser. No. 09/107,845 filed on Jun. 30, 1998. This application is further related to the following co-pending U.S. patent applications, which are hereby incorporated herein by reference: Ser. No. 09/178,075, filed on Oct. 23, 1998; Ser. No. 09/282,140, filed Mar. 31, 1999.

FIELD OF THE INVENTION

The present invention relates, in general, to a method of controlling the excision of tissue in biopsy instruments and, more particularly, to a method of controlling the rotation and translation of a cutter in a biopsy instrument.

BACKGROUND OF THE INVENTION

The diagnosis and treatment of patients with cancerous tumors, premalignant conditions, and other disorders has long been an area of intense investigation. Non-invasive methods for examining tissue include palpation, X-ray, magnetic resonance imaging (MRI), computed tomography (CT), and ultrasound imaging. When a physician suspects that tissue may contain cancerous cells, a biopsy may be done using either an open procedure or a percutaneous procedure. For an open procedure, a scalpel is used to create a large incision in the tissue to provide direct viewing and access to the tissue mass of interest. The entire mass (excisional biopsy) or a part of the mass (incisional biopsy) may then be removed. In most percutaneous biopsy procedures, a needle-like instrument is inserted through a very small incision to access the tissue mass of interest and obtain a tissue sample for later examination and analysis.

Aspiration and core sampling are two percutaneous methods for obtaining a portion of tissue from within the body. In an aspiration procedure, tissue is fragmented into pieces and drawn through a fine needle in a fluid medium. The method is less intrusive than most other sampling techniques, however, it has limited application since the structure of tissue excised by aspiration is destroyed leaving only individual cells for analysis (cytology) and not the tissue structure for analysis (pathology). In core biopsy, a core or fragment of tissue is obtained in a manner, which preserves both the cells and the structure for histological examination. The type of biopsy used depends mainly on various factors, and no single procedure is ideal for all cases. Core biopsy, however, is very useful in a number of conditions and is widely used by physicians.

Examples of core sampling biopsy instruments are described in U.S. Pat. Nos. 5,562,822 and 5,769,086 (both issued to Ritchart, et al), and in U.S. patent application Ser. No. 09/107,845 filed on Jun. 30, 1998. Another example of a core sampling biopsy instrument is the biopsy instrument now marketed by Ethicon Endo-Surgery, Inc., Cincinnati, Ohio, under the trade name MAMMOTOME. Each of these instruments is a type of image-guided, percutaneous, coring, breast biopsy instrument, which uses a vacuum for retrieving tissue samples. A physician uses these instruments to capture "actively" (using the vacuum) tissue prior to severing it from the body. In particular, in these biopsy instruments, tissue is drawn into a port at the distal end of a piercing element, hereinafter referred to as a piercer. A cutting element, hereinafter referred to as a cutter, is rotated and advanced through a lumen of the piercer past the port. As the cutter advances through the port, it severs the tissue drawn into the port from the surrounding tissue. While the cutter is generally rotated using some type of motor, it may be advanced either manually or automatically. In the MAMMOTOME instrument, the surgeon manually moves the cutter back and forth by lateral movement of a knob mounted on the outside of the instrument. Once the cutter is in place, proximal to the tissue port, further lateral movement of the knob is prevented and the cutter is advanced through the tissue port to sever tissue by twisting the knob. This arrangement is advantageous because the surgeon is able, through tactile and/or audible feedback, to determine whether the cutter is effectively cutting tissue or if there is a problem, such as binding or stalling. The surgeon may then adjust the speed at which the cutter is moved through the tissue, stop the cutter or back the cutter away from the tissue.

As described in U.S. Pat. Nos. 5,562,822 and 5,769,086, the translation of the cutter may be automated to facilitate the procedure. However, if the procedure is automated as described in those references, the surgeon loses the benefit of the tactile feedback, which results when the cutter is advanced manually. It is generally desirable to ensure that the rotational speed of the cutter does not drop below a predetermined speed in order to sever cleanly the tissue sample from surrounding tissue and to avoid damage to the tissue sample. Automating translation of the cutter will, to some extent, eliminate the tactile feedback that the surgeon gets from moving the cutter manually. The advantageous method of automatically measuring and controlling the rotation and translation of the cutter is not described for either of the devices in the '822 or '086 patents. This automatic control method could be used, for example, to prevent the cutter from advancing when the opening is blocked by something other than tissue. Such an automatic control method could also be used to ensure that the cutter rotates at an optimal speed to ensure proper cutting of the tissue and to prevent the cutter rotational speed from dropping below a predetermined limit.

Another advantage of a core sampling biopsy device being used with an automatic control method is that the operator would be able to perform the surgical procedure in less time than with a motorized device having no automatic control method. Since core sampling biopsy devices extract tissue samples from deep within the body of the surgical patient, the penetrating element, or piercer, for accessing the tissue, is necessarily long. The driven element, or cutter, must translate from the proximal end of the piercer to the distal end in order to collect the tissue sample. Then the cutter transports the tissue sample from the distal end of the piercer to the proximal end, which is outside the body of the patient. As the cutter is actually cutting through tissue and collecting the tissue sample, the translational speed of the cutter should be maintained in an optimal range. But for all other portions of cutter translation, the translational speed of the cutter may be relatively high without detrimental effects. Thus the time required for obtaining each tissue sample might be reduced. Since many tissue samples may be extracted from the patient during a typical surgical procedure, the accumulated time saved could be significant, providing obvious benefit for both the surgeon and the patient.

A core sampling, surgical instrument with a needle guiding stage of a stereotactic mammography biopsy system is disclosed in U.S. Pat. No. 5,830,219 by Bird, et al. In this instrument, the driven element (hereinafter referred to as a cutter) translates to cut tissue captured in the distal end of the instrument. This instrument couples feedback from an optical encoder with a microprocessor to calculate cutting resistance so that if the cutter encounters, for example, a dense tissue mass causing the cutter rotation to decrease, additional electrical current is automatically provided to the cutter motor to resume the desired cutter rotational speed. The encoder also provides information to the microprocessor to control automatically the angular stroke of the cutter as it oscillates between the clockwise and counterclockwise directions. This closed loop cutter control method is described in '219 as being provided only for when the cutter is in the cutting portion of its axial travel.

An alternate control method, however, to deal with an increase in cutting resistance (due to encountering dense tissue or obstructions) is to slow incrementally the translational speed of the cutter until a desired cutter rotational speed is resumed. If the cutter cannot penetrate the obstruction and the desired rotational speed cannot be resumed despite reducing translational speed, then the translation of the cutter could be completely halted and an error message, for example, could be transmitted to the operator. This alternate control method would have an advantage of preventing damage to the biopsy instrument because the tissue sample is obtained less aggressively due to the slowed advance of the cutter through the tissue, or else the cutter translation is completely halted if the obstruction is impenetrable.

Another advantage for reducing the cutter translational speed rather than increasing the cutter rotational speed in response to an increase in rotational resistance on the cutter is that smaller, less powerful, and less expensive motors could be used to drive the cutter. Both the translation motor for advancing the cutter and the rotation motor for rotating the cutter may be smaller because the overall rate at which work would be done on the tissue by the cutter could be reduced. Using smaller, lighter weight motors would also facilitate their incorporation into the handheld portion of the biopsy instrument. As described in pending U.S. patent application Ser. No. 09/178,075, the motors can be remotely located in a separate control unit and operationally connected to the handheld portion of the biopsy instrument by at least one rotatable shaft. In such a biopsy instrument, using small motors would be advantageous in allowing the use of small diameter, lightweight, rotatable shafts. In addition to the cost savings realized in the manufacture of the device, the biopsy instrument could be more hand manipulatable by the operator during the surgical biopsy procedure.

It is also advantageous to use both types of responses to increased rotational resistance on the cutter. That is, a single control method that combines a method for decreasing cutter translational speed and a method for increasing cutter rotational speed in response to decreasing cutter rotation may be used. For example, if the cutter encounters an obstruction in tissue and the cutting resistance rises sharply, the electrical current to the cutter rotational motor may automatically be increased by a predetermined amount. If the cutter rotational speed is measured and compared to a desired, predetermined cutter rotation speed, and it is determined that the cutter rotational speed is still not high enough, than the cutter translational speed may be decreased by a predetermined amount. These steps could be repeated automatically until the tissue sample is obtained, or until certain operational thresholds (minimal translation speed, maximum current to rotation motor, for example) are reached. By using such a combined method in response to increasing rotational resistance on the cutter, the cutter rotational and translational motors may be smaller than when using a method to modify cutter rotation alone.

When an operator uses a handheld instrument operationally connected to a remotely located motor by a flexible, rotatable shaft, the operational configuration of the rotatable shaft may affect the efficiency of the mechanical energy transmitted to the handpiece. For example, if it is necessary for the operator to hold the handheld instrument during the surgical procedure so that the flexible, rotatable shaft is sharply curved, the resistance to rotation of the rotatable shaft is higher than if the rotatable shaft was in a straight configuration. Also, when the operator manipulates the probe of the instrument to penetrate into the tissue mass of interest, a bending moment may be unavoidably applied to the piercer of the probe, increasing the rotational resistance of the cutter which is constructed coaxially in close alignment with the piercer. There also may be additional mechanical losses, for example, due to wear or misalignment of power transmission components. Therefore, it would be advantageous to be able to measure the total, rotational resistance before the cutter encounters tissue, so that the cutter rotation may be increased to the desired, predetermined rotational speed for cutting tissue.

For an automated, handheld biopsy device, the cutter rotation and translation motors may be mounted in a remote unit in order to minimize the overall size and weight of the handpiece. As described in U.S. patent application Ser. No. 09/178,075, each motor may be operationally connected with the cutter of the handpiece of the biopsy device by a flexible, rotatable shaft. A tradeoff associated with using a flexible, rotatable shaft is that the shaft may twist along its length, or "wind" under loading. A measurement on the proximal end of the rotatable shaft of the angular position of the shaft may vary from that on the distal end. Since the precise number of shaft rotations may be used to calculate axial position of the cutter, it is desirable to incorporate a high-resolution means within the biopsy device to measure and compensate for the twisting of the flexible, rotatable shaft operationally connected to the remotely located translation motor.

What is needed is a core sampling biopsy device having a control method and apparatus that allows the cutter translational speed to be automatically responsive to cutting resistance caused by obstructions or dense tissue encountered by the cutter. What is further needed is a core sampling biopsy device having a control method and apparatus that allows the cutter rotational speed to be automatically responsive to total rotational resistance on the cutter before and during the cutting of tissue. What is further needed is a core sampling biopsy device having a control method and apparatus that allows the cutter translational speed to be automatically responsive to cutter translational position so that surgical procedure time may be reduced. What is finally needed is a high-resolution means within the biopsy device to measure and compensate for the twisting of the flexible, rotatable shaft operationally connected to the remotely located translation motor.

SUMMARY OF THE INVENTION

The present invention is a control apparatus for removing at least one tissue sample from a surgical patient using a surgical biopsy device. The biopsy device comprises an elongated piercer having a piercer lumen extending therethrough, and a cutter rotatably and axially positionable relative to said piercer. The piercer has a port for receiving and transferring the tissue sample into the piercer lumen. The biopsy device further comprises a rotation motor for rotating the cutter and a translation motor for translating the cutter in the axial direction.

In one embodiment of the present invention, the control apparatus comprises a computing device for the coordinated control of the rotation and translation motors. The control apparatus further comprises a first sensor operationally connected to the rotation motor for supplying a rotation signal to the computing device for measuring the rotational speed of the cutter. The control apparatus further comprises a second sensor operationally connected to the translation motor for supplying a translation signal to the computing device for measuring the translational position and translational speed of the cutter. The control apparatus further comprises a first driver for driving the translation motor in response to a translation command from the computing device, and a second driver for driving the rotation motor in response to a rotation command from said computing device. The control apparatus automatically modifies the rotational speed and the translational speed of the cutter in response to the translational position and rotational resistance acting on the cutter.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 7A is a top view in section of the probe assembly and a distal portion of the holster, revealing the cutter in the third position wherein the distal end of the cutter is immediately proximal to the port;

FIG. 7B is a top view in partial section of the distal end of the probe assembly with the port on the distal end of the piercer open and the distal end of the cutter in the third position immediately proximal to the port;

FIG. 8A is a top view in section of the probe assembly and a distal portion of the holster illustrating the cutter in the fourth, fully deployed position;

FIG. 8B is a top view in partial section of the distal end of the probe assembly illustrating the distal end of the cutter in the fourth position distal to the port at the distal end of the piercer;

DETAILED DESCRIPTION OF THE INVENTION

Figure 1:
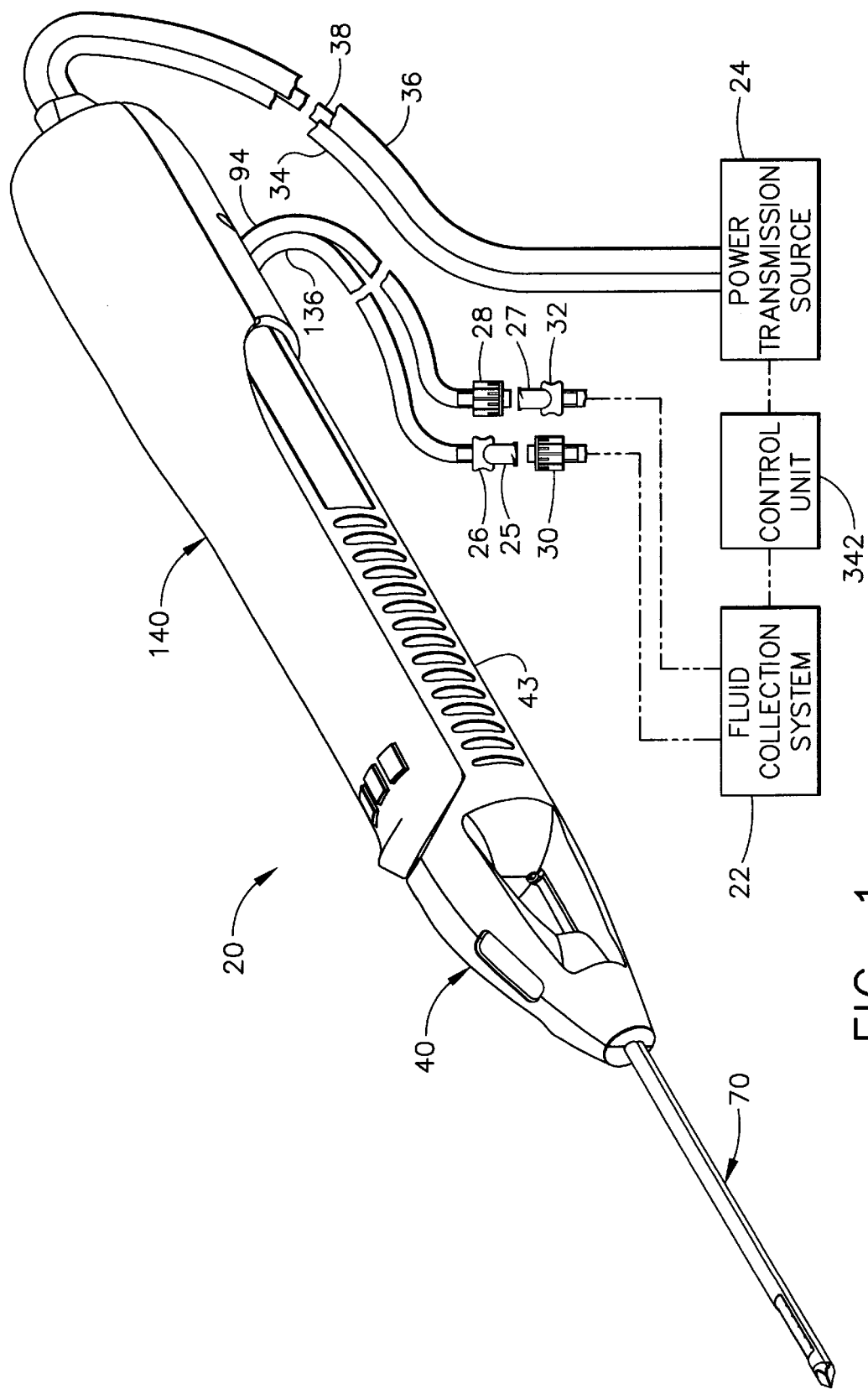
FIG. 1 is an isometric view of the present invention, a biopsy instrument, which includes a handpiece for the collection of soft tissue.

FIG. 1 shows a core sampling biopsy instrument comprising a probe assembly 40, a holster 140, a fluid collection system 22, a control unit 342, and a power transmission source 24. Probe assembly 40 is detachably connected to holster 140. Together they constitute a lightweight, ergonomically shaped, hand manipulatable portion referred to as a handpiece 20. Probe assembly 40 includes a piercer 70 extending distally from a hollow handle 43. Probe assembly 40 is fluidly connected to fluid collection system 22 by a first vacuum tube 94 and a second vacuum tube 136. First and second vacuum tubes are detachably connected to fluid collection system 22 by a first connector 27 and a second connector 25, respectively. First connector 27 has a male portion 32 and a female portion 28 attached to first vacuum tube 94. Second connector 25 has a female portion 30 and a male portion 26 attached to second vacuum tube 136. Connector portions, 26, 28, 30, and 32 are attached in this manner to prevent the accidental switching of first and second tubes, 136 and 94, to fluid collection system 22. Holster 140 includes a first rotatable shaft 34, a second rotatable shaft 36, and a control cord 38. First and second rotatable shafts, 34 and 36, are preferably flexible so that the operator may easily manipulate handpiece 20 with one hand. Control cord 38 operationally connects the handpiece 20 to power transmission source 24 and control unit 342.

Since handpiece 20 is manipulated by the operator's hand rather than by an electromechanical arm, the operator may steer the tip of handpiece 20 with great freedom towards the tissue mass of interest. The surgeon has tactile feedback while doing so and can thus ascertain, to a significant degree, the density and hardness of the tissue being encountered. In addition, handpiece 20 may be held approximately parallel to the chest wall of the patient for obtaining tissue portions closer to the chest wall then may be obtained when using a instrument mounted to an electromechanical arm.

Those skilled in the art may appreciate that a mount or "nest" could be provided to hold handpiece 20 securely to the movable arm of an X-ray stereotactic table. This would provide the operator with the option to use handpiece 20 to access the tissue mass within the surgical patient in much the same manner as was described earlier for using the MAM-MOTOME instrument. This versatility may be advantageous to the operator, for example, in a situation where the handheld imaging device was temporarily not available for use, and it would be necessary to use the X-ray stereotactic table.

Figure 2:
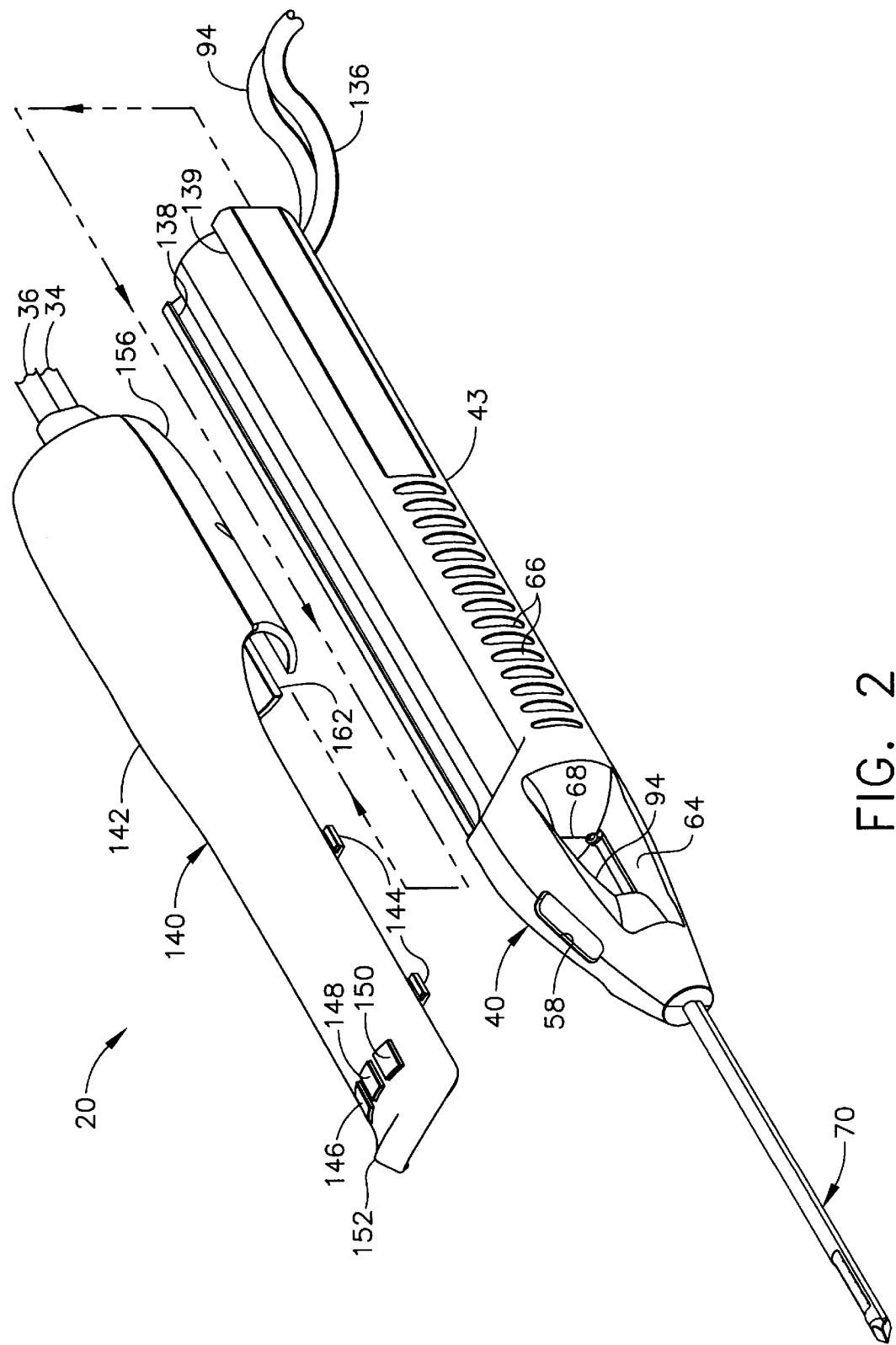
FIG. 2 is an isometric view of the handpiece showing a probe assembly prior to attachment to a holster.

FIG. 2 shows holster 140 and probe assembly 40 separated. A pair of tabs 144 project laterally from each side of a holster upper shell 142, and insert into right and left undercut ledges, 138 and 139 respectively, of hollow handle 43 of probe assembly 40. A plurality of indentations 66 is provided on handle 43 to improve the operator's grip on the instrument. A tube slot 162 in lower shell 156 of holster 140 provides clearance for first and second vacuum tubes, 94 and 136. A cutter forward switch 146 for moving a cutter 96 (see FIG. 3) in the distal direction, a cutter reverse switch 148 for moving cutter 96 in the proximal direction, and a vacuum switch 150, are mounted in the distal portion of holster 140 so that the operator can use handpiece 20 with a single hand. One-handed operation allows the other hand to be free, for example, to hold an ultrasonic imaging device. A ridge 152 on the distal end of holster 140 is provided to assist the operator in grasping handpiece 20 and in operating switches 146, 148, and 150.

Still in FIG. 2, probe assembly 40 includes a window 58 so that a portion of first vacuum tube 94 may be viewed. First and second vacuum tubes, 94 and 136, are made from a flexible, transparent or translucent material, such as silicone tubing. This enables visualization of the material flowing through the tubes, 94 and 136. By having window 58 in probe assembly 40, the operator can see the flow in first vacuum tube 94 without needing to look away from the tissue into which piercer 70 is inserted. A transverse opening 68 is provided in the distal end of hollow handle 43 which allows access from either side to a tissue sampling surface 64. The tissue extracted from the surgical patient is retrieved by the operator or by an assistant from tissue sampling surface 64.

Figure 3:
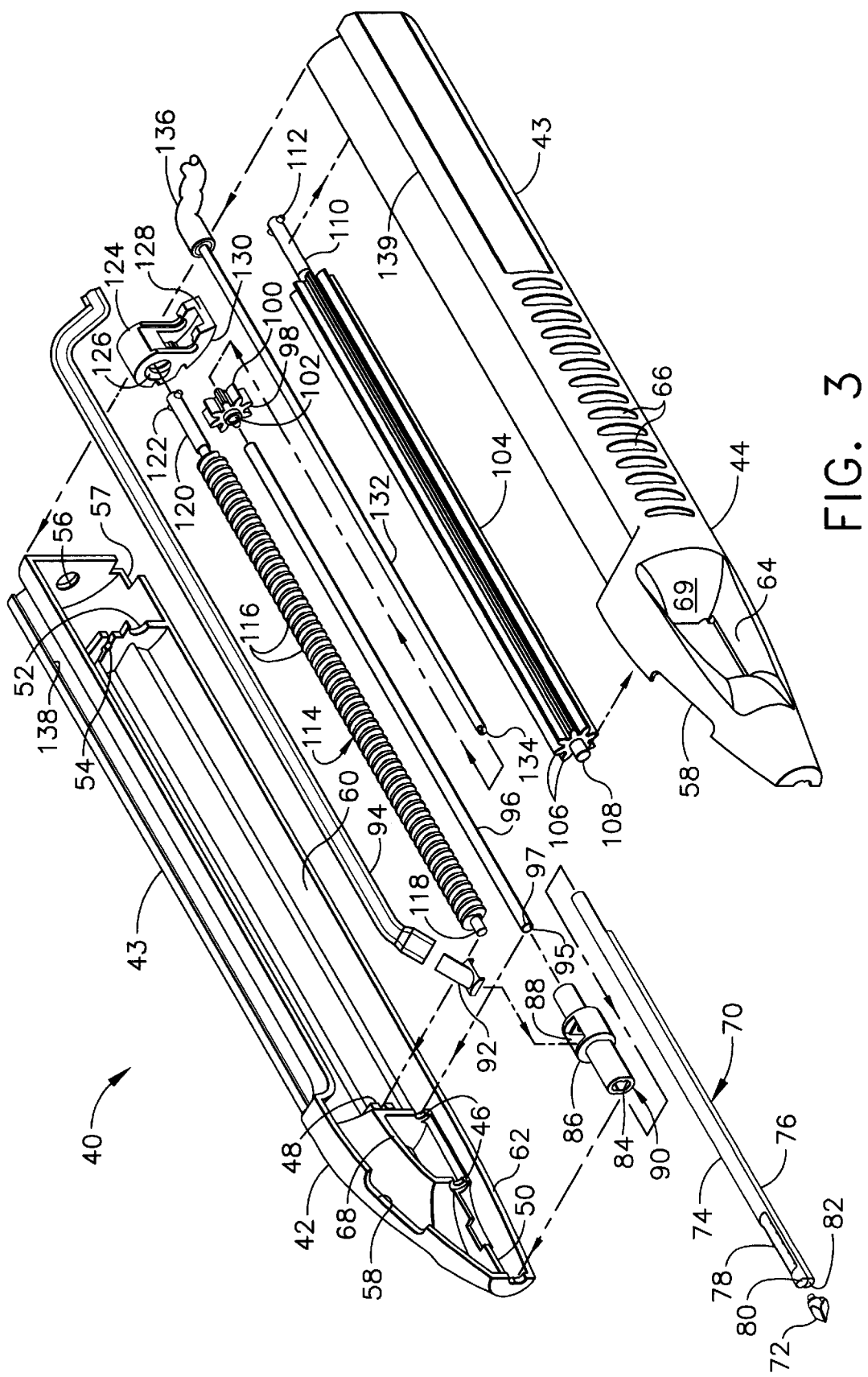
FIG. 3 is an exploded isometric view of the probe assembly illustrated in FIG. 2.

FIG. 3 is an exploded isometric view of probe assembly 40. Handle 43 is formed from a right handle shell 42 and a left handle shell 44, each injection molded from a rigid, biocompatible plastic such as polycarbonate. Upon final assembly of probe assembly 40, left and right handle shells, 42 and 44, are joined together by ultrasonic welding along a joining edge 62, or joined by any of several other methods well known in the art. Probe assembly 40 comprises piercer 70 having an elongated, metallic piercer tube 74 and a piercer lumen 80. On the side of the distal end of piercer tube 74 is a port 78 for receiving the tissue to be extracted from the surgical patient. Joined alongside piercer tube 74 is an elongated, tubular, metallic vacuum chamber tube 76 having a vacuum lumen 82. Piercer lumen 80 is in fluid communication with vacuum lumen 82 via a plurality of vacuum holes 77 (see FIG. 6B) located in the bottom of the "bowl" defined by port 78. These vacuum holes 77 are small enough to remove the fluids but not large enough to allow excised tissue portions to be removed through first vacuum tube 94 (see FIG. 2) which is fluidly connected to vacuum chamber 76. A metallic, sharpened distal end 72 is attached to the distal end of piercer 70. It is designed to penetrate soft tissue such as the breast of a female surgical patient. In this embodiment, sharpened distal end 72 is a three-sided, pyramidal-shaped point, although the tip configuration may also have other shapes.

Still referring to FIG. 3, the proximal end of piercer 70 is attached to a union sleeve 90 having a longitudinal bore 84 through it, a widened center portion 86, and a transverse opening 88 through widened center portion 86. Union sleeve 90 is mounted between left and right handle shells, 44 and 42 respectively, on a pair of union sleeve ribs 50 (only the rib in the right handle shell is visible) projecting from each handle shell. An elongated, metallic, tubular cutter 96 is axially aligned within longitudinal bore 84 of union sleeve 90 and piercer lumen 80 of piercer 70 so that cutter 96 may slide easily in both the distal and proximal directions. A pair of cutter guides 46 are integrally molded into each of handle halves, 42 and 44, to slidably retain cutter 96 in an co-axially aligned position with the proximal end of piercer tube 74. Cutter 96 has a cutter lumen 95 through the entire length of cutter 96. The distal end of cutter 96 is sharpened to form a cutter blade 97 for cutting tissue held against cutter blade 97 as cutter 96 is rotated. The proximal end of cutter 96 is attached to the inside of a cutter gear bore 102 of a cutter gear 98. Cutter gear 98 may be metallic or polymeric, and has a plurality of cutter gear teeth 100, each tooth having a typical spur gear tooth configuration as is well known in the art.

Still in FIG. 3, cutter gear 98 is driven by an elongated drive gear 104 having a plurality of drive gear teeth 106 designed to mesh with cutter gear teeth 100. The function of drive gear 104 is to rotate cutter gear 98 and cutter 96 as they translate in both longitudinal directions. Drive gear 104 is preferably made from a metal such as stainless steel. A distal drive axle 108 projects from the distal end of drive gear 104 and mounts into an axle support rib (not visible) molded on the inside of left handle shell 44. A gear shaft 110 projects from the proximal end of drive gear 104 and is supported by a gear shaft support rib (not visible) also molded on the inside of left handle shell 44. A left cross pin 112 is attached to the proximal end of gear shaft 110 as a means for rotationally engaging drive gear 104.

Still referring to FIG. 3, a carriage 124 is provided to hold cutter gear 98 and to carry cutter gear 98 as it is rotated in the distal and proximal directions. Carriage 124 is preferably molded from a rigid polymer and is cylindrically shaped with a threaded bore 126 through it and with a carriage foot 130 extending from its side. Foot 130 has a recess 128 formed into it for rotatably holding cutter gear 98 in the proper orientation for cutter gear teeth 100 to mesh properly with drive gear teeth 106. Carriage 124 is attached via threaded bore 126 to an elongated screw 114, which is parallel to drive gear 104. Screw 114 has a plurality of conventional lead screw threads 116 and is preferably made from a stainless steel. The rotation of screw 114 in one direction causes carriage 124 to move distally, while the reverse rotation of screw 114 causes carriage 124 to move proximally. In turn cutter gear 98 moves distally and proximally according to the direction of the screw rotation and cutter 96 is advanced or retracted. In this embodiment, screw 114 is shown with a right hand thread so that clockwise rotation (looking from the proximal to distal direction) causes carriage 124 to translate in the proximal direction. It is also possible to use a left-hand thread for screw 114 as long as provisions are made to do so in control unit 342. A distal screw axle 118 and a proximal screw shaft 120 project from the distal and proximal ends, respectively, of screw 114. Distal screw axle mounts rotatably in a distal screw support 48 of right handle shell 42 while proximal screw shaft 120 mounts rotatably in a proximal screw support 54, also in right handle shell 42. A right cross pin 122 is attached to the proximal end of screw shaft 120 as a rotational engagement means.

Figure 4:
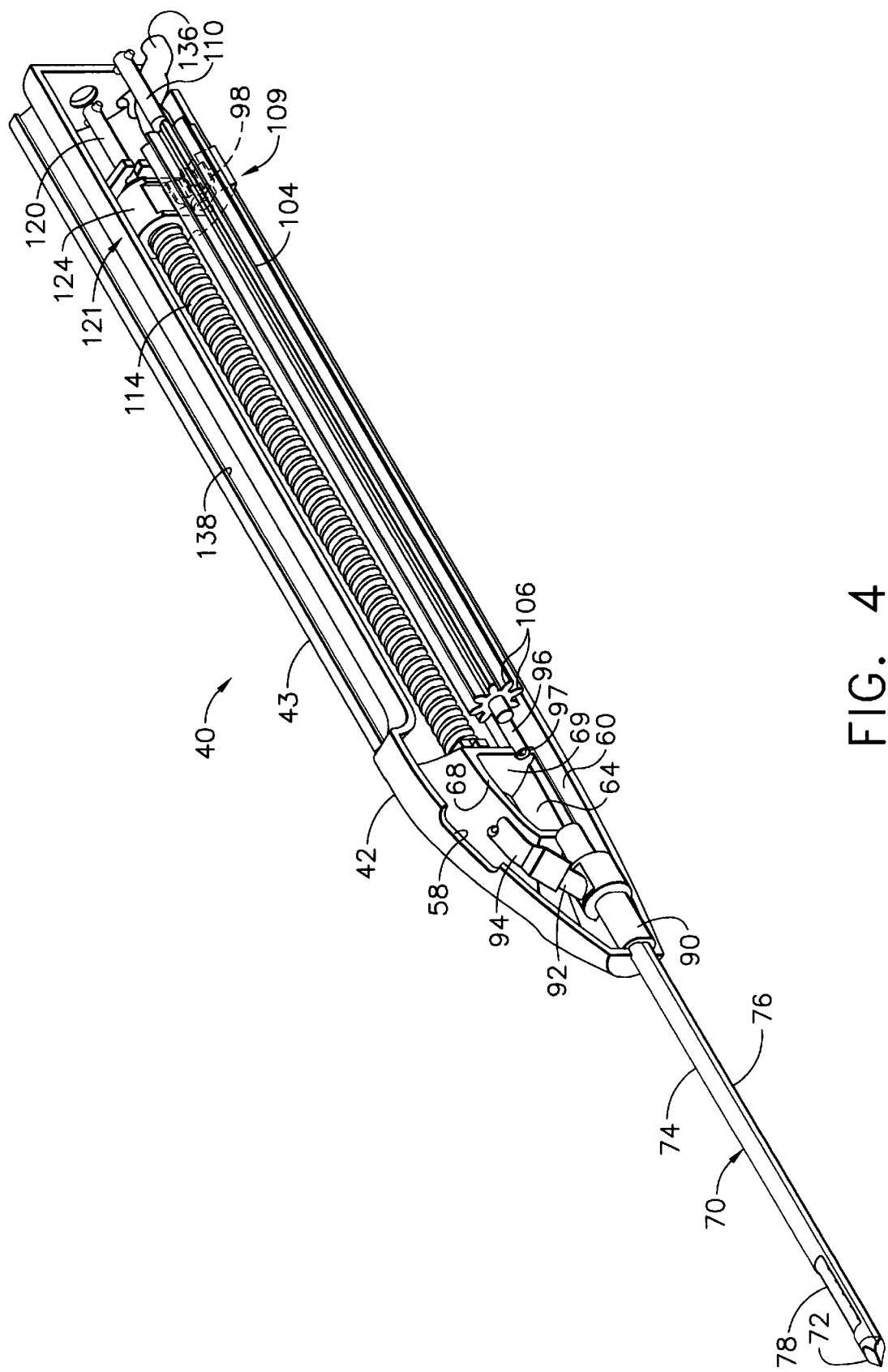
FIG. 4 is an isometric view of the probe assembly of FIG. 2 with the left handle shell removed to reveal the internal components.

At this point in the detailed description, it is important to point out that during operation of the present invention, cutter 96 translates in either direction between a fully retracted position just proximal to tissue sampling surface 64 and a fully deployed position just distal to port 78 (see FIG. 4). There are key intermediate positions along the length (about six inches for this particular embodiment) of the cutter translation. When the distal end of cutter 96 reaches each of these positions, important adjustments to either the cutter rotational speed (sometimes referred to simply as rotation speed) or the cutter translational speed (sometimes referred to simply as translation speed), or both, are made automatically. For the embodiment of the biopsy device described herein, there are four positions along the length of the cutter translation. At these positions, signals to control unit 342 are sent in order to make appropriate adjustments to cutter rotational speed and/or cutter translational speed. To facilitate description of the cutter positions, they are to be understood as actually the positions of cutter blade 97 on the distal end of cutter 96. These four cutter positions are the following: a first position where cutter 96 is just proximal to the tissue sampling surface 64 (see FIG. 6B); a second position where cutter 96 is just distal to the tissue sampling surface 64 (in FIG. 6B, the cutter blade 97 would be located to the left of tissue sampling surface 64 instead of to the right); a third position where cutter 96 is just proximal to port 78 (see FIG. 7B); and a fourth position where cutter 96 is just distal to port 78 (see FIG. 8B). These four cutter positions are given by way of example although numerous other cutter positions may be used in the present invention for automatically signaling adjustments to cutter rotational speed and/or translational speed. These four positions are sometimes referred to as a position one, a position two, a position three, and a position four. They are also referred to as a position 1, a position 2, a position 3, and a position 4.

It is possible to have more or less than the four cutter positions identified, depending on what is programmed into control unit 342. For example, a fifth position of the cutter 96 may be at a location about 2 mm proximal to the port 78. The rotation of the cutter 96 may then be accelerated to the appropriate speed (1450 rpm, for example) slightly before the cutter 96 encounters tissue prolapsed into port 78. Likewise, a sixth position of the cutter 96 may be at a location about 2 mm distal to port 78 so that the cutter 96 is decelerated after it has traversed the entire length of the port 78.

Now referring again to FIG. 3, the distal end of first vacuum tube 94 is attached to a polymeric vacuum fitting 92 which inserts tightly into transverse opening 88 of the union sleeve 90. This allows the communication of fluids in piercer lumen 80 to fluid collection system 22. First vacuum tube 94 is contained within the hollow handle 43 in an open space above screw 114 and drive gear 104, and exits the distal end of hollow handle 43 through an opening 57. Second vacuum tube 136 is fluidly attached to the proximal end of an elongated, metallic, tubular tissue remover 132. Second vacuum tube 136 exits the hollow handle 43 alongside first vacuum tube 94 out the opening 57. A strainer 134 is attached to the distal end of tissue remover 132 to prevent the passage of fragmented tissue portions through it and into fluid collection system 22. Tissue remover 132 inserts slidably into tubular cutter 96. During operation of the biopsy instrument, tissue remover 132 is always stationary and is mounted between a pair of proximal supports 52 on the inside of the right and left handle shells, 42 and 44 respectively. When cutter 96 is fully retracted to the first position, the distal end of tissue remover 132 is approximately even with the distal end of cutter 96. The distal end of cutter 96 when at its first, fully retracted position, is slightly distal to a vertical wall 69 which is proximal and perpendicular to tissue sampling surface 64.

In FIG. 3, a right access hole 56 is shown in the proximal end of right handle shell 43. Right access hole 56 provides access to the proximal end of the screw 114 for operational engagement to power transmission source 24. Similarly, a left access hole (not shown) is provided in left handle shell 44 to provide access to the proximal end of drive gear 104 for operational engagement with power transmission source 24.

Figure 9:
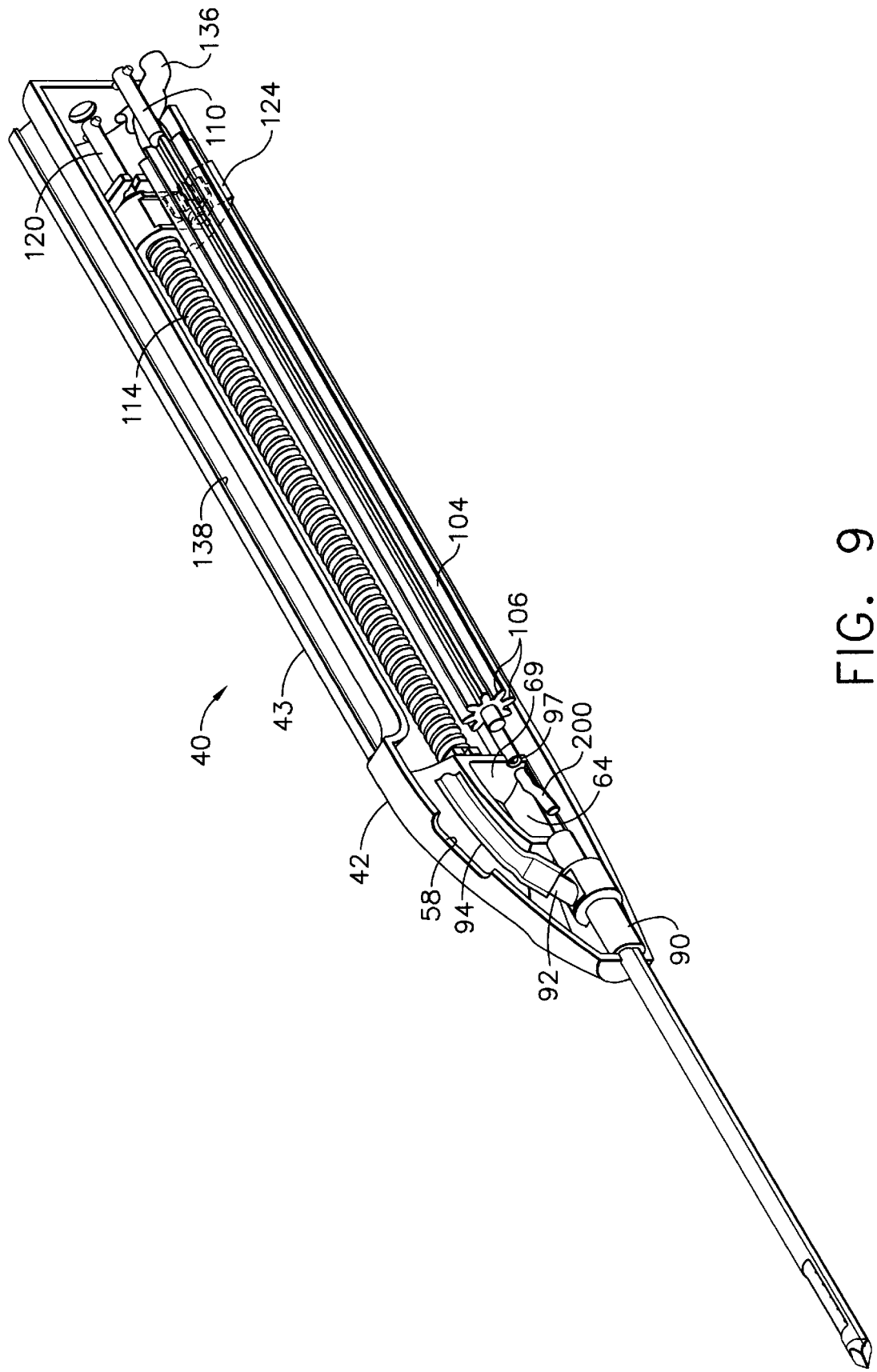
FIG. 9 is an isometric view of the probe assembly with the left handle shell removed, showing the cutter in the first position, with a tissue sample shown deposited onto a tissue sampling surface.

Tissue remover 132 has two functions. First, it helps to evacuate fluids contained in piercer lumen 80. This is accomplished by the attachment of second vacuum tube 136 to the proximal end of tissue remover 132. Since the distal end of tissue remover 132 is inserted into piercer lumen 80, piercer lumen 80 is fluidly connected to fluid collection system 22. Second, tissue remover 132 removes tissue from cutter 96 as follows. When a tissue sample is taken, cutter 96 advances to the fourth position just distal to port 78, and a severed tissue sample 200 (see FIG. 9) is captured within cutter lumen 95 in the distal end of cutter 96. Then cutter 96 translates to the first position so that cutter blade 97 is just distal to tissue sampling surface 64. At this position of cutter 96, the distal end of tissue remover 132 (which is always stationary) is approximately even with the distal end of cutter 96. Therefore, any tissue portion of significant size contained within cutter lumen 95 is pushed out of cutter lumen 95 and onto tissue sampling surface 64, as is shown in FIG. 9. The operator or an assistant may then retrieve tissue sample 200.

Now turning to FIG. 4, an isometric view of probe assembly 40 with left handle shell 44 removed reveals the placement of the components described for FIG. 3. Part of first vacuum tube 94 has also been removed for clarity. Carriage 124 is shown in the fully retracted position so that cutter 96 is also at the fully retracted or first position. Cutter blade 97 is slightly distal to vertical wall 69 on handle 43. Foot 130 of carriage 124 is adapted to slide along a carriage guide surface 60 on the inside bottom of hollow handle 43.

As shown in FIG. 4, a cutter translational transmission 121 includes carriage 124, screw 114, and screw shaft 120. A cutter rotational transmission 109 includes drive gear 104, cutter gear 98, and gear shaft 110.

Figure 5:
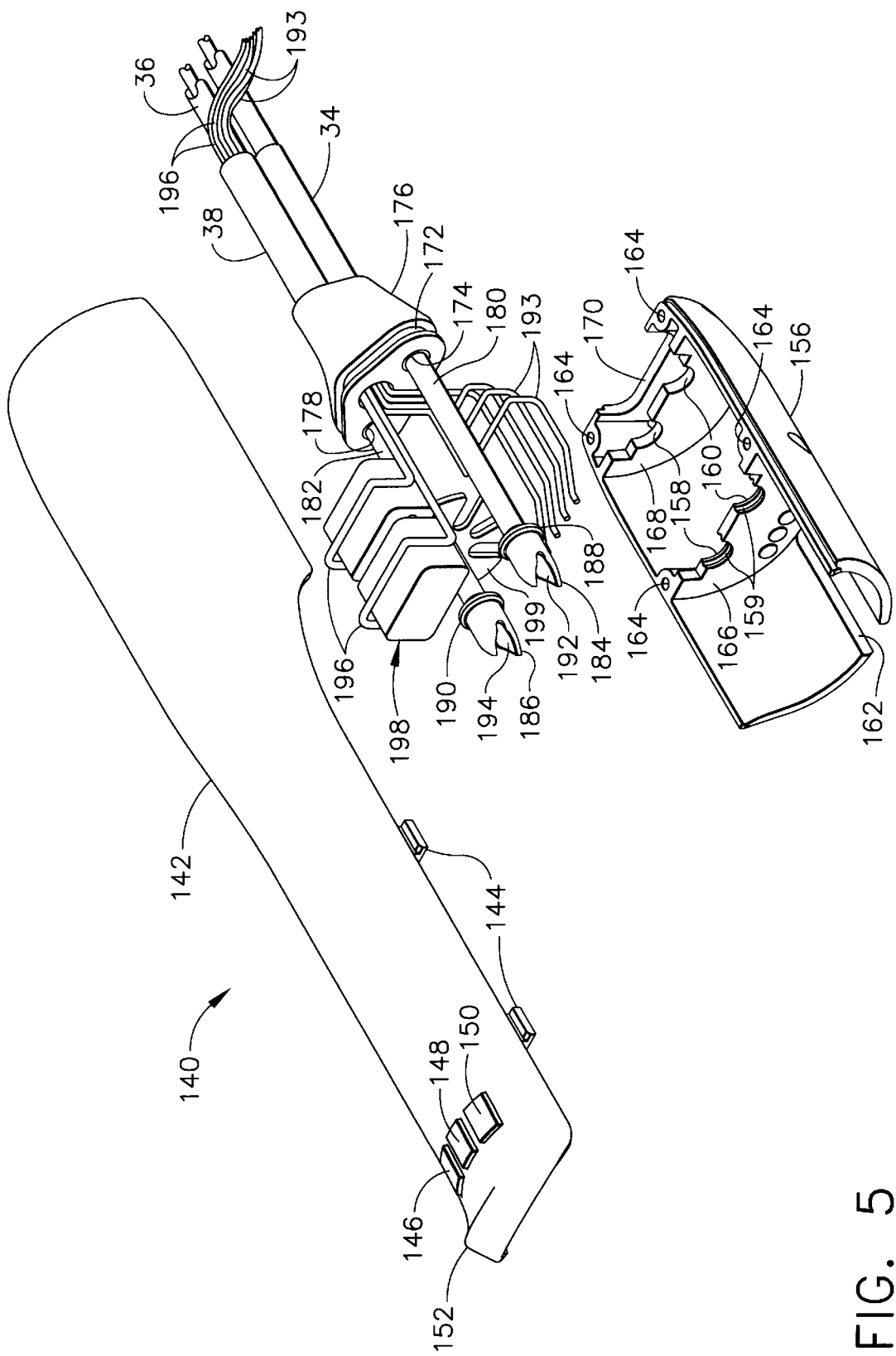
FIG. 5 is an exploded isometric view of the holster illustrating a non-encased rotation sensor mounted on a screw drive shaft.

FIG. 5 is an exploded isometric view of holster 140. A holster upper shell 142 and a holster lower shell 156 are each injection molded from a rigid, biocompatible plastic such as polycarbonate. Upon final assembly, the shells are joined together by screws (not shown) or other types of fasteners well known in the art, into a plurality of alignment holes 164. A gear drive shaft 180 and a screw drive shaft 182 are contained within the proximal, enclosed portion of holster 140. These shafts extend from a grommet 176 which has a groove 172 for retainably mounting onto shell edge 170 of both holster upper and lower shells, 142 and 156, respectively. Grommet 176 rotatably attaches first rotatable shaft 34 to screw drive shaft 182 and second rotatable shaft 36 to gear drive shaft 180. First rotatable shaft 34 rotatably inserts into a left bore 174 of grommet 176. Second rotatable shaft 36 rotatably inserts into a right bore 178. Grommet 176 also provides a strain-relieved attachment of control cord 38 to holster 140.

Still referring to FIG. 5, gear drive shaft 180 is supported rotatably upon a pair of gear drive mounts 160 formed into a first wall 166 and a second wall 168 of the inside of holster shells, 142 and 156. Screw drive shaft 182 is likewise supported rotatably on screw drive mounts 158. A left coupler 184 is attached to the distal end of drive gear shaft 180 and has a left coupler mouth 192 for rotational engagement with left cross pin 112 attached to gear shaft 110. When probe assembly 40 shown in FIG. 4 is attached to holster 140, gear shaft 110 becomes rotatably engaged to gear drive shaft 180. This may be seen more clearly in FIG. 6A. Similarly, screw drive shaft 182 has a right coupler 186 with a mouth 194, which rotatably engages with cross pin 122 of screw shaft 120. Each of the left and right couplers, 184 and 186, have a coupler flange, 188 and 190, which rotatably insert into thrust slots 159 formed into the corresponding portions of drive mounts 158 and 160. Coupler flanges, 188 and 190, bear the translational loading of drive shafts, 180 and 182.

Still referring to FIG. 5, holster 140 further includes an non-encased, rotation sensor 198 for providing an electronic signal to control unit 342 to be described later. A suitable example of an non-encased rotation sensor 198 is an optical encoder, Part Number HEDR-81002P, available from the Hewlett-Packard Corporation. In this first embodiment, non-encased rotation sensor 198 is mounted within the inside of holster upper shell 142 and in a position directly above screw drive shaft 182. A fluted wheel 199 is attached to screw drive shaft 182 and extends in front of a light emitting diode contained within non-encased rotation sensor 198. As fluted wheel 199 rotates, the interrupted light beams are electronically detected and transmitted back to control unit 342 to provide information about the rotational speed of screw drive shaft 182. By counting the number of screw rotations from the beginning of operation, the instantaneous axial translation position and speed in either direction of the cutter 96 may be calculated by control unit 342. Non-encased rotation sensor leads 196 pass through grommet 176 and are part of the bundle of conductors within control cord 38.

Holster 140 shown in FIG. 5 has forward, reverse, and vacuum switches, 146, 148, and 150 respectively, mounted on the inside of holster upper shell 142. Switches 146, 148, and 150 are electronically connected to a plurality of conductors 193 contained in control cord 38. Vacuum switch 150 operates fluid communication with fluid collection system 22 and also sets control unit 342 to respond to various commands as described later. Reverse switch 148 operates the movement of cutter 96 in the proximal direction and sets control unit 342 to respond to various commands. Forward switch 150 operates the movement of cutter 96 in the distal direction and sets control unit 342 to respond to various commands. The physical locations of switches, 146, 148, and 150 on handpiece 20 are not restricted to the locations depicted in FIG. 2. Other embodiments of handpiece 20 of the present invention may incorporate certain ergonomic or other considerations, and switches 146, 148, and 150 may be located elsewhere. In addition, switches 146, 148, and 150 may be of varying shapes and colors, or have varying surface treatments, so as to distinguish from one another, and to assist the operator in differentiating each one from the others either by tactile or visual identification.

As already described, FIGS. 6A through 8A depict three of the four positions of the cutter 96 during the operation of the present invention as embodied in the prior FIGS. 1–5. The three positions are most easily distinguished by observing the relative positions of the carriage 124 (which moves together with cutter 96) and cutter blade 97 on the distal end of cutter 96.

Figure 6A:
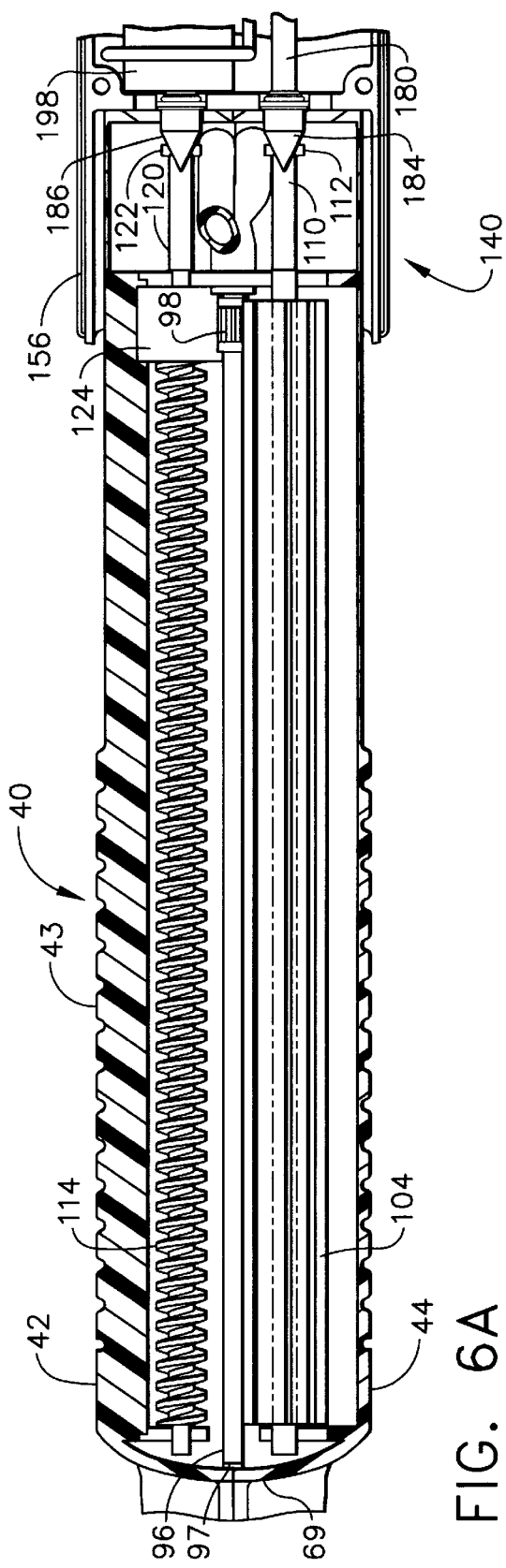
FIG. 6A is a top view in section of the probe assembly and a distal portion of the holster, revealing a cutter in a first, fully retracted position.
Figure 6B:
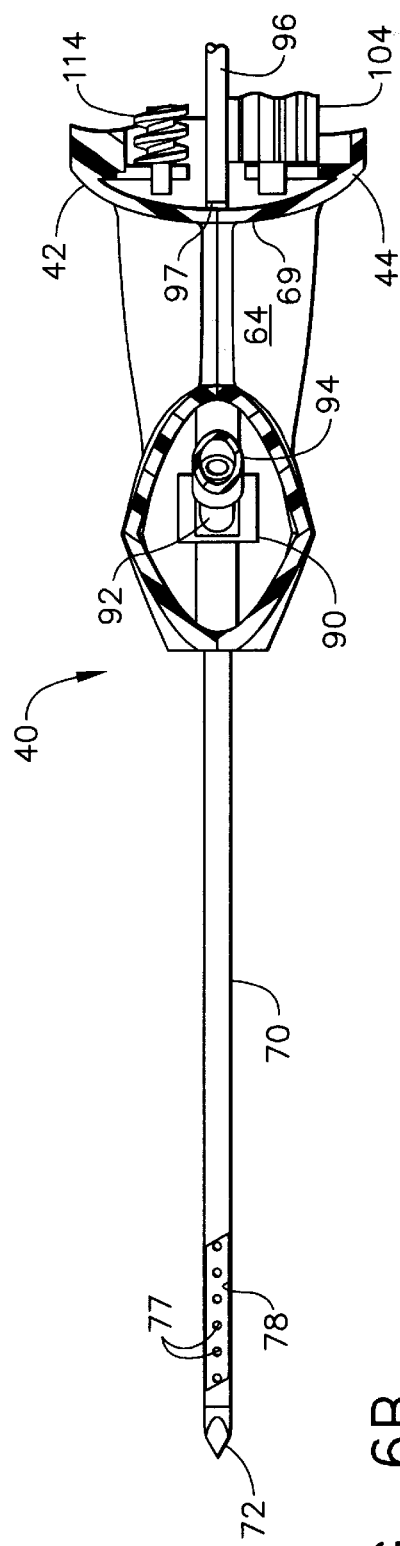
FIG. 6B is a top view in partial section of the distal end of the probe assembly illustrating the cutter in the first, fully retracted position wherein the port on the distal end of the piercer is open.

In FIGS. 6A and 6B, cutter 96 is at the first position. Carriage 124 begins its translation on the proximal ends of drive gear 104 and screw 114. Cutter blade 97 is shown to be immediately proximal to tissue sampling surface 64. In the first position, tissue sample 200 may be retrieved from tissue-sampling surface 64 (see FIG. 9).

In FIGS. 7A and 7B, cutter 96 is at the third position. Carriage 124 is shown to have translated to the intermediate position that is a short distance from the distal ends of screw 114 and drive gear 104. Cutter blade 97 is shown by hidden lines to be located just proximal to port 78. Vacuum holes 77 are open to port 78 so that soft tissue adjacent to port 78 can be pulled into port 78 when first vacuum tube 94 is fluidly connected to the vacuum of fluid collection system 22.

FIGS. 8A and 8B show cutter 96 at the fourth position. Carriage 124 is located near the distal ends of screw 114 and drive gear 104. Cutter blade 97 is shown now (by hidden lines) to be distal to port 78 and to be covering vacuum holes 77. The tissue pulled into port 78 will have been severed by the rotating, advancing cutter blade 97 and stored inside cutter lumen 95 of the distal end of cutter 96. When cutter 96 retracts back to the first position as shown in FIGS. 6A and 6B, tissue sample 200 may be retrieved as shown in FIG. 9.

Figure 10:
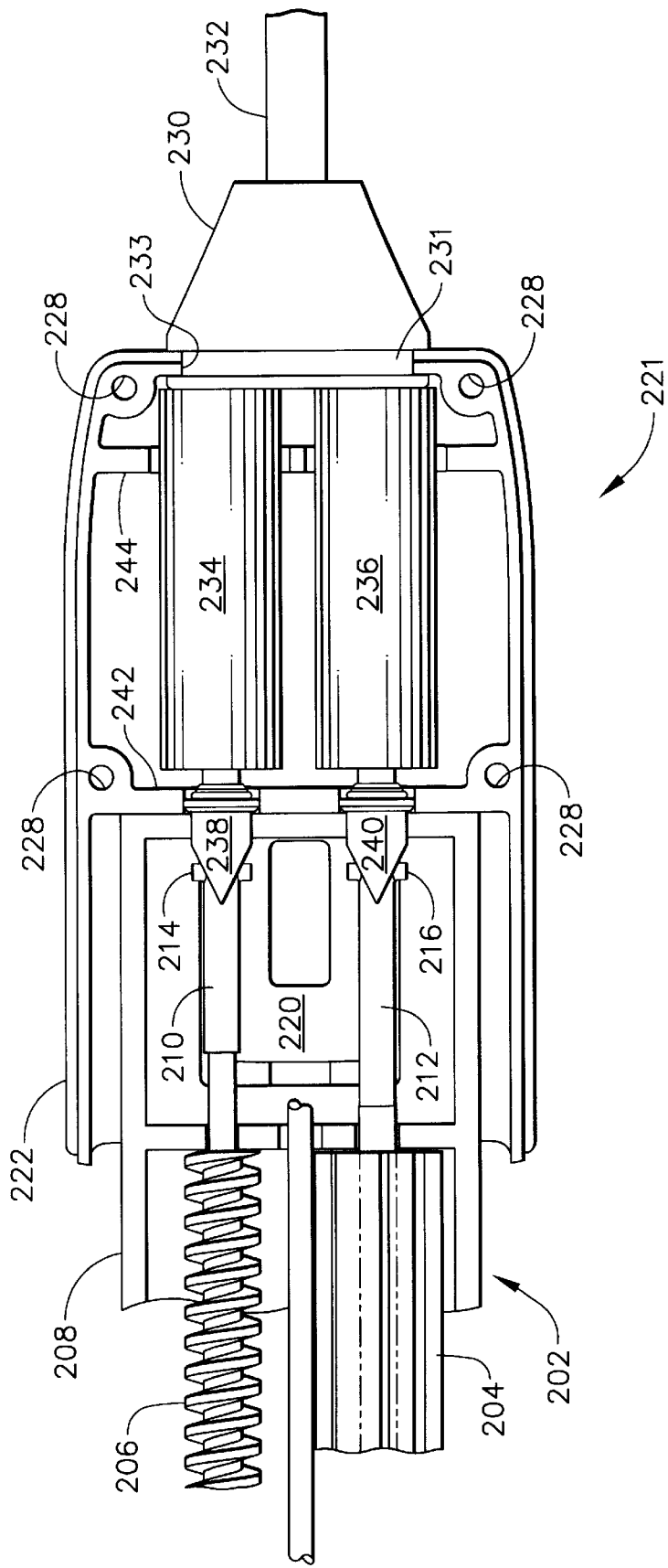
FIG. 10 is a partial top view of a further embodiment of the present invention wherein a first and a second motor are contained within a handheld holster rather than in a remotely located control unit as for the embodiment of FIG. 5, and wherein the holster upper shell and the probe assembly upper shell have been removed to reveal the internal components.

FIG. 10 shows a further embodiment of the present invention, including an integrally motorized holster 221. The main difference from the embodiment of holster 140 shown in FIG. 5 is that integrally motorized holster 221 contains a first brushless, electric motor 234 and a second, brushless electric motor 236. A suitable example for first and second brushless, electric motors, 234 and 236, is Part Number B0508-050, available from Harowe Servo Controllers, Incorporated. In the embodiment of FIG. 10, rotatable shafts 34 and 36 have been eliminated so that only a control/electrical power cord 232 is required to electrically connect integrally motorized holster 221 to power transmission source 24 and control unit 342 (see FIG. 1). A holster lower shell 222 has a first wall 242 and a second wall 244, which are spaced apart and adapted to support the pair of brushless, electric motors, 234 and 236, in a side-by-side arrangement. The use of brushless, electric motors, 234 and 236, eliminates the need for a separate rotation sensor to be mounted in the drive train of one or both of a screw 206 and a drive gear 204 as was described for holster 140 shown in FIG. 5. As for holster 140 of FIG. 5, when a probe assembly 202 is attached to integrally motorized holster 221, a right coupler 238 rotationally engages a right cross pin 214 of a screw shaft 210. A left coupler 240 rotationally engages a left cross pin 216 of a gear shaft 212. An attachment slot 233 in the holster shell 222 retains a grommet 230 having a grommet groove 231. Fastener holes 228 are provided to fasten holster lower shell 222 to a holster upper shell (not shown) using screws or other types of fasteners well known in the art.

Another difference of integrally motorized holster 221 shown in FIG. 10 from holster 140 shown in FIG. 5 is that probe assembly 202 comprises a lower shell 208 and an upper shell (not shown). Hollow handle 43 of holster 140 shown in FIG. 5, however, is divided vertically into left and right shells, 44 and 42 respectively. This arrangement facilitates the mounting of brushless motors, 234 and 236, and additional features described next.

Figure 11:
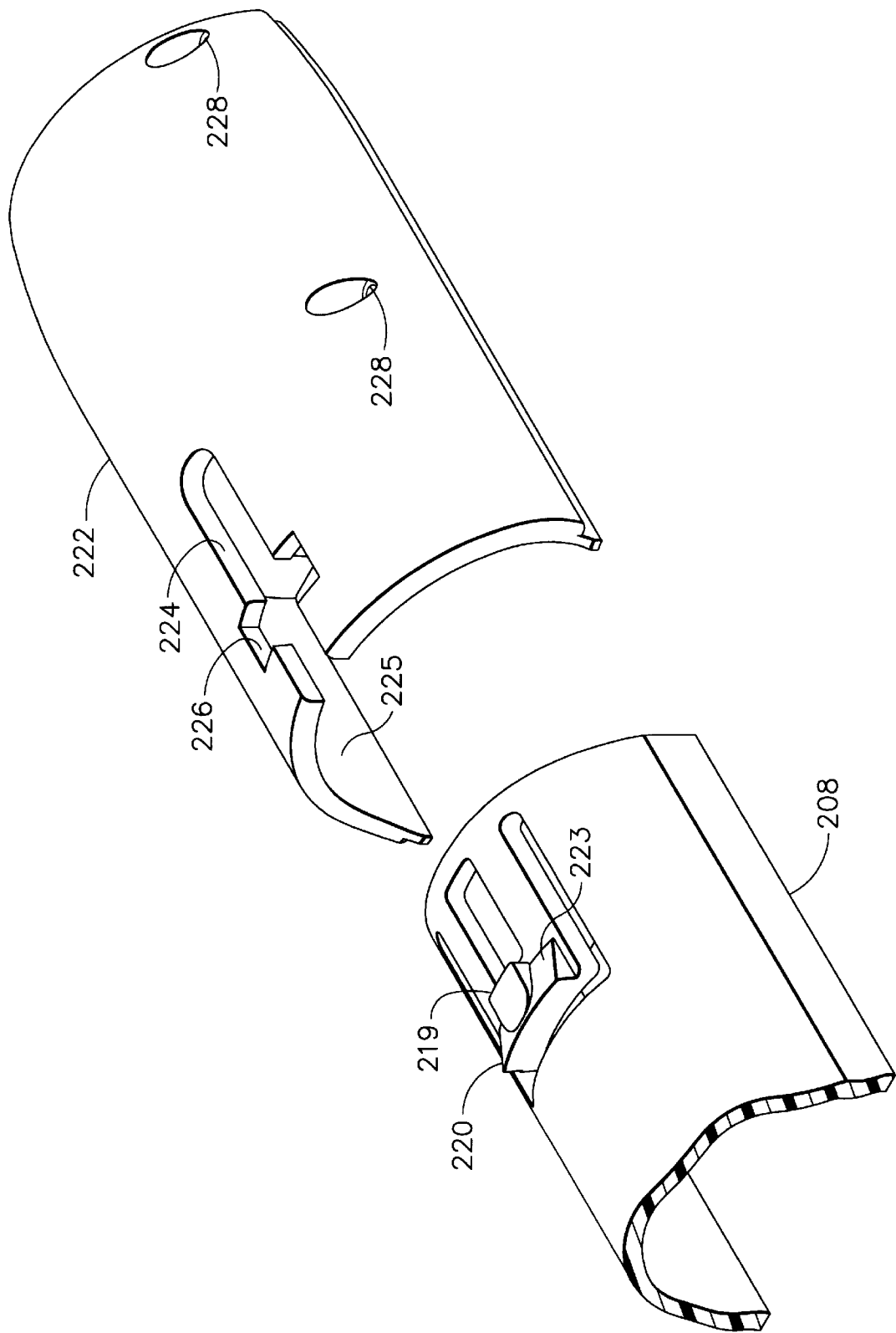
FIG. 11 is an isometric view of the holster and probe assembly lower shells shown in FIG. 10, wherein the holster lower shell includes a slot for the removable attachment to a latch on the probe assembly lower shell.
Figure 12:
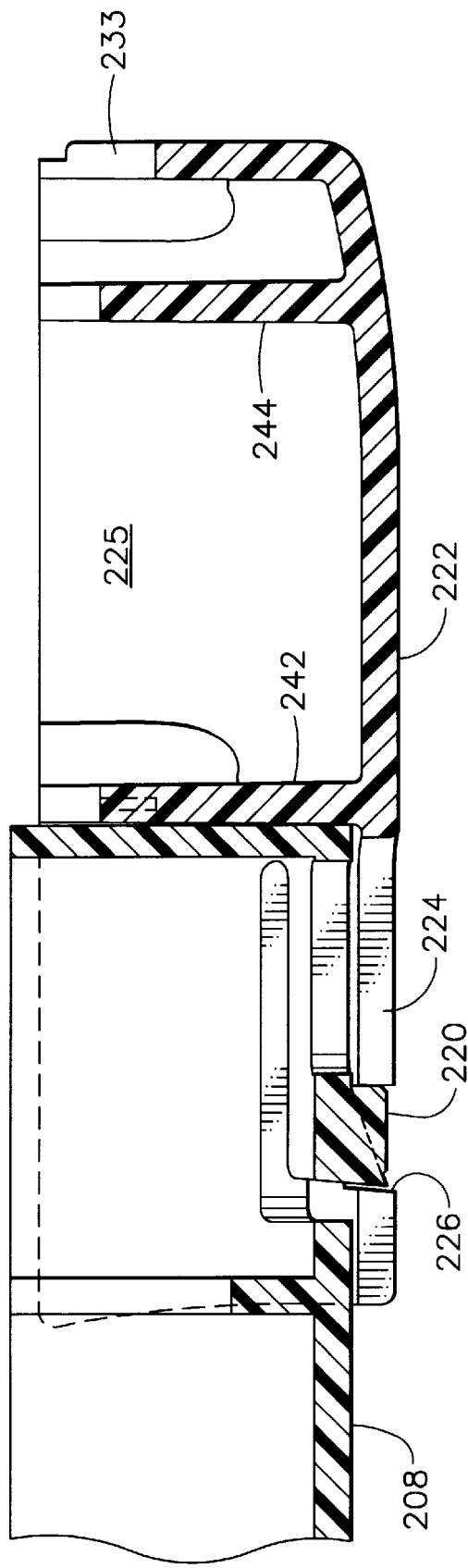
FIG. 12 is a longitudinal section of the holster and probe assembly lower shells of FIG. 11, illustrating their removable attachment to each other.

FIG. 11 shows an isometric view of probe lower shell 208 and holster lower shell 222 of integrally motorized holster 221 illustrated in FIG. 10. The view in FIG. 11 is upside-down with respect to the view in FIG. 10 in order to show a probe latch 220 molded into probe lower shell 208. Probe latch 220 is a cantilever beam and can be deflected downwards by a force applied to a latch ramp surface 223. Probe latch 220 further comprises a latch projection 219 for insertion into a holster slot 224 as probe assembly 202 is inserted into integrally motorized holster 221. Ramp surface 223 is deflected downwards by interaction with an inside surface 225 of holster shell 222 and retainably snaps into a slot key 226 when probe assembly 202 is fully inserted into integrally motorized holster 221. By engaging probe latch 220 in this way, the left and right couplers, 240 and 238, rotationally engage to drive gear shaft 212 and screw shaft 210, respectively, as shown in FIG. 10. To remove probe assembly 202 from integrally motorized holster 221, the operator presses on projection 219 while pulling them apart. FIG. 12 shows a longitudinal section through the center axis of probe lower shell 208 and holster lower shell 222 of FIG. 11 for when they are fully attached together.

Figure 13:
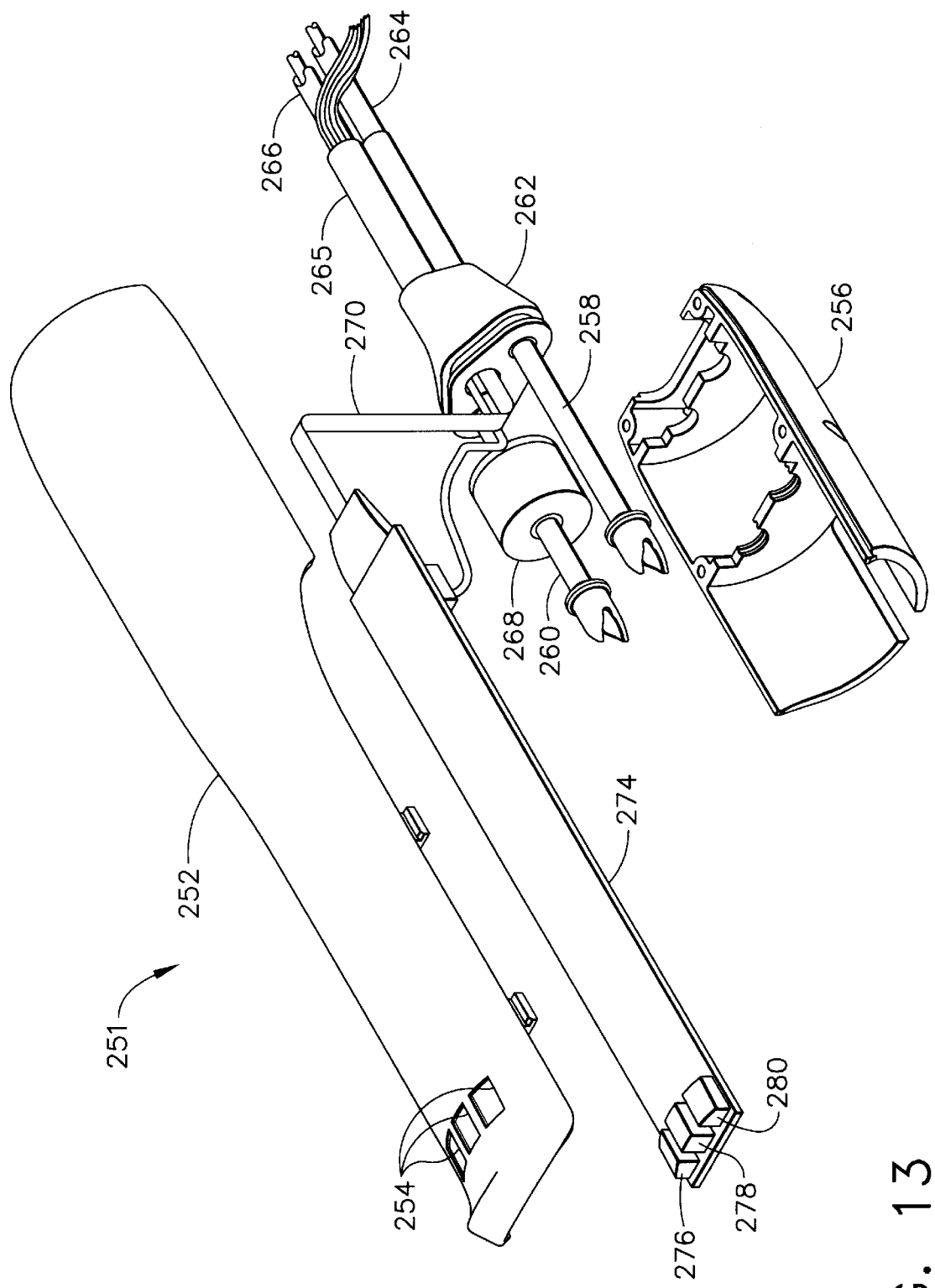
FIG. 13 is an exploded isometric view of a further embodiment of the holster illustrated in FIG. 5, wherein the further embodiment includes the three switches being mounted on a switch board electrically connected by a ribbon cable to the control cord (instead of the three switches being electrically connected to the control cord by discrete switch conductors as illustrated in FIG. 5), and wherein the further embodiment includes an encased rotation sensor rather than the non-encased rotation sensor of the embodiment illustrated in FIG. 5.

FIG. 13 is an exploded isometric view of a further embodiment of the present invention that includes a switchboard 274 integrally mounted inside of a switch board-modified holster 251. Switch board-modified holster 251 may be used with probe assembly 40 shown in FIGS. 1–4. A first rotatable shaft 264 and a second rotatable shaft 266 are each attached by a grommet 262 to a drive shaft 258 and a screw shaft 260, respectively. Rotatable shafts, 264 and 266, are preferably flexible too, in order for switch board-modified holster 251, together with probe assembly 40 (see FIG. 2), to be easily manipulatable with one hand. An encased rotation sensor 268 (also referred to as a third sensor) is shown mounted on a screw shaft 260. A suitable example for encased rotation sensor 268 is a miniature optical encoder, which is commercially available as Model Number SEH17 from CUI Stack, Incorporated. It is electrically connected to a switchboard 274 which mounts to the inside of the holster upper shell 252. Switchboard 274 also has a ribbon cable 270 containing a plurality of conductors for conveying electronic information to and from control unit 342. Switch board 274 has mounted on its distal end, three switches, 276, 278, and 280, for operation of the present invention in the same manner as described for holster 140 of FIG. 5: a vacuum switch 280 for fluidic connection to the vacuum of fluid collection system 22; a forward switch 276 for the forward movement of cutter 96; and a reverse switch 278 for the reverse movement of cutter 96. Switches 276, 278 and 280 project through three switch openings 254 of holster upper shell 252. A holster lower shell 256 attaches to upper shell 252 as in the other embodiments to enclose the components of the proximal portion of holster 251. It is well known in the art that controls for a surgical instrument such as described in the embodiments herein may be incorporated into a foot operable mechanism in order to free the hands of the operator.

Figure 14:
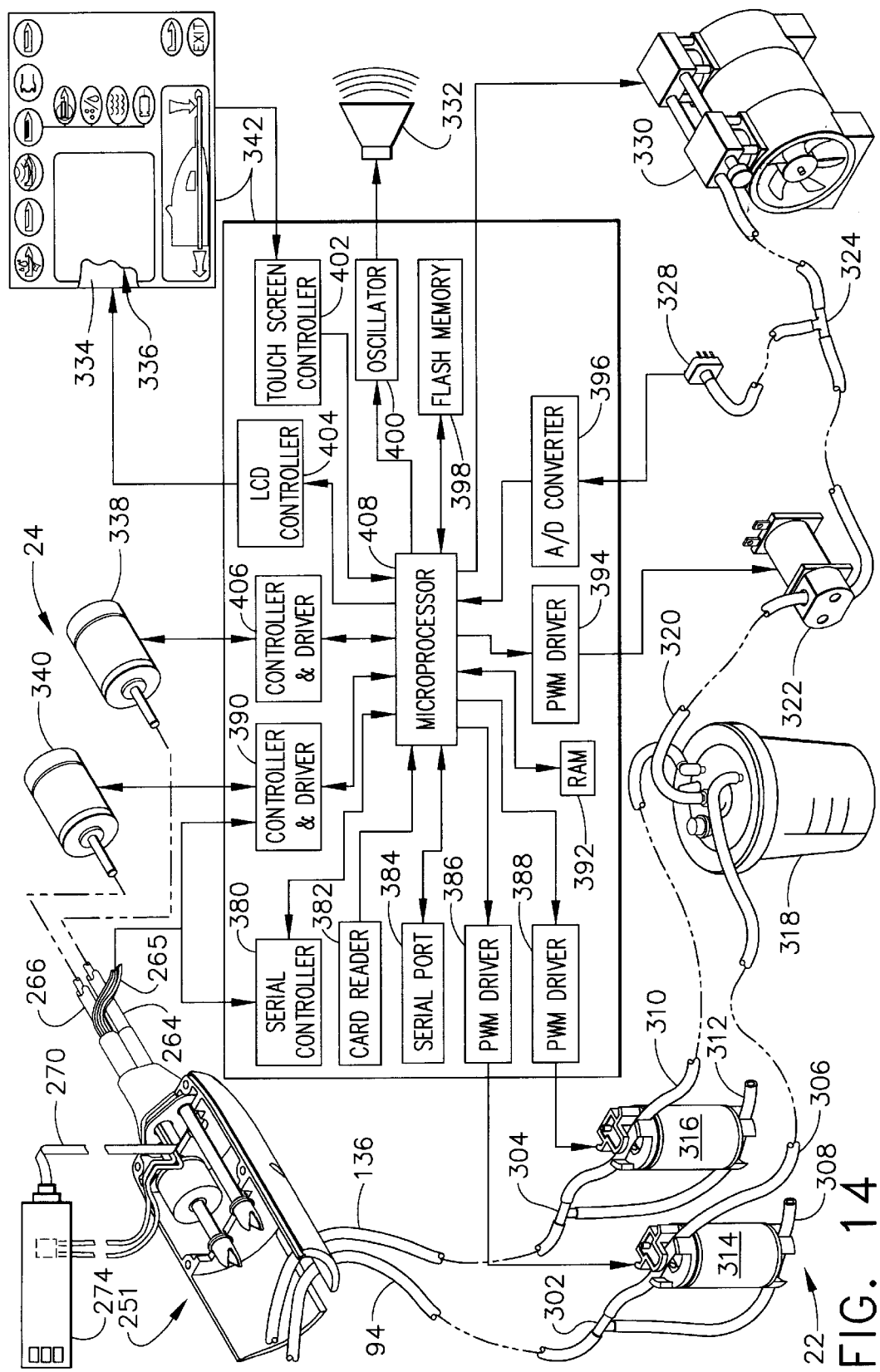
FIG. 14 is a schematic diagram of a control unit according to the present invention.
Figure 16A:
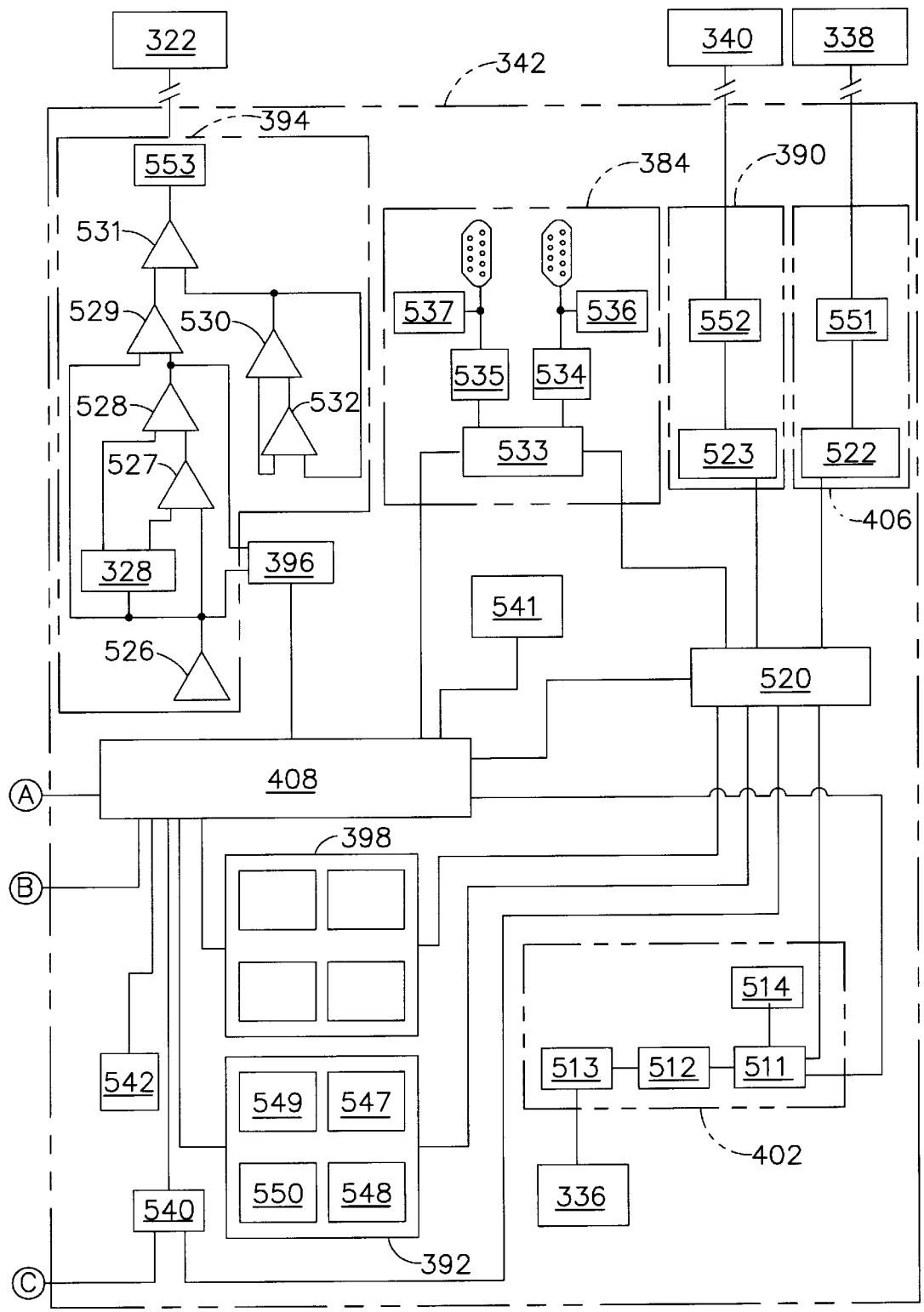
FIG. 16A is the first of two portions of a divided schematic diagram of the control unit components illustrated in FIG. 14.
Figure 16B:
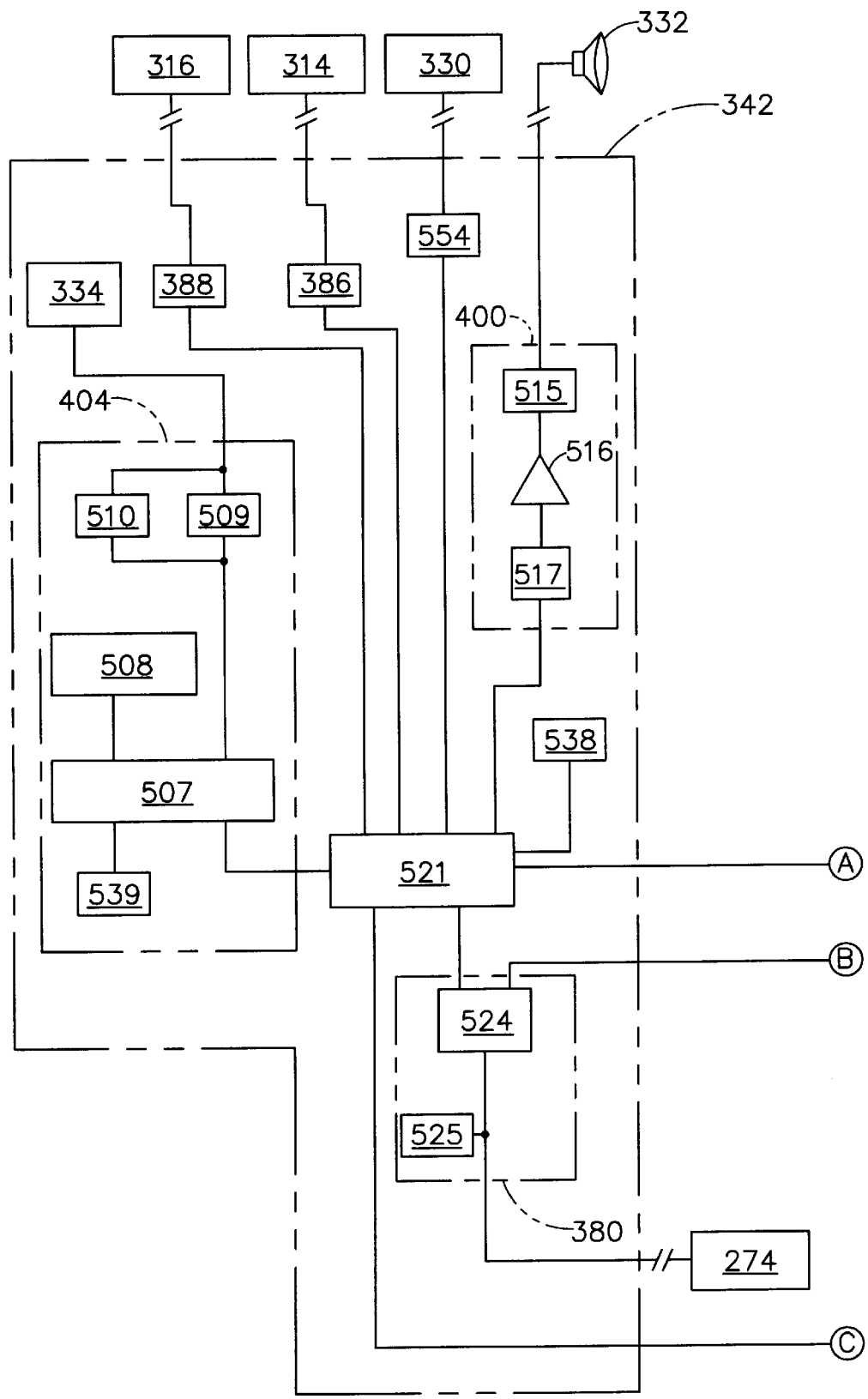
FIG. 16B is the second of two portions of the divided schematic diagram of the control unit components illustrated in FIG. 14.

FIG. 14 is a schematic diagram which illustrates the interconnection of the electromechanical components of the biopsy device to control unit 342. FIG. 14 illustrates the biopsy device illustrated in FIG. 1 and comprises control unit 342, fluid collection system 22, power transmission source 24, and handpiece 20 (see FIG. 1). A more detailed schematic diagram illustrating the elements of control unit 342 is shown in FIGS. 16A and 16B and will be described later. All of the components of FIG. 14 may be packaged into a portable, wheeled unit, and moved from room to room such as in a physician's office. Handpiece 20 (see FIG. 1), as described earlier, may be mounted to a stereotactic table already in the room, or handheld and used in combination with a handheld imaging device such as a handheld ultrasonic imager. Each time the biopsy device is used for a new patient, a new sterile probe assembly 40 may be used in handpiece 20.

In particular, FIG. 14 illustrates the interconnection of switchboard modified holster 251 with control unit 342, and the connection of power transmission source 24 to control unit 342. In the embodiment of the invention illustrated in FIG. 14, power transmission source 24 comprises a rotation motor 338 and a translation motor 340. Rotation motor 338 and translation motor 340 transmit rotational power to switchboard-modified holster 251 via first and second rotatable shafts, 264 and 266, respectively. An example of a motor which is suitable for either rotation motor 338 or translation motor 340 is available from Micro Motors Electronics, Incorporated, as DC Micro Motors Series 3863, with integral, miniature optical encoder, Part Number SHE 17. Rotation motor 338 has an integral rotation sensor also referred to as a first sensor. Translation motor 340 has an integral rotation sensor also referred to as a second sensor.

By having encased rotation sensor 268, as shown in FIG. 14, mounted in switchboard modified holster 251, it is possible for control unit 342 to calculate the amount of twisting along the length of first rotatable shaft 266 by comparing the output of the encoder of rotation motor 338 to the output of encased rotation sensor 268. Since the number of revolutions of rotatable shaft 266 is used to determine where cutter 96 is located axially, this twisting could cause significant error, especially if rotatable shaft 266 is very long. This error could result, for example, in cutter 96 not stopping immediately when translation motor 340 is turned off, because first rotatable shaft 266 is continuing to "unwind". As a result, control unit 342 uses the signals from the integral rotation sensor (also referred to as the first sensor) of translation motor 340 and rotation sensor 268 to calculate accurately the axial position of cutter 96.

Second rotatable shaft 264 runs parallel to first rotatable shaft 266 between control unit 342 and holster 251. The mechanical efficiency of either shaft in transmitting rotation from the respective motor to holster 251 varies to some degree with the orientation of the rotatable shaft. If for example, it is necessary during the surgical procedure for the operator to drape first and second rotatable shafts, 266 and 264, so that they are bent significantly, then there will be more frictional energy losses than if the shafts were straight. In one embodiment of the present invention, if the initial current supplied to rotation motor 338 is not sufficient to attain a predetermined cutter rotational speed, the current to rotation motor 338 increases until a desired rotational speed is reached. The rotation sensor integrated into rotation motor 338 provides feedback signals to control unit 342, so that the compensating current can be supplied to rotation motor 338. Once the desired rotational speed is reached, the current to rotation motor 338 is "locked" until the cutter 96 reaches position four at the end of its translation. This electrical compensation occurs for each time cutter 96 translates between the second and third positions, before cutter 96 begins to cut tissue. This allows for variations in the way rotatable shafts, 264 and 266, are oriented for each time the operator positions the biopsy instrument for collecting a tissue sample.

Referring now to fluid collection system 22 shown in FIG. 14, fluid collection system 22 comprises a first valve 314, a second pinch valve 316, a fluid collection canister 318, a regulator valve 322, a pressure sensor 328, and a vacuum pump 330. These components are interconnected to each other, control unit 342, and probe assembly 40 (FIG. 1) as follows. First vacuum tube 94 comes from probe assembly 40 (FIG. 1), and is attached to a first vacuum Y-connector 302 which is fluidly connected to a first upper line 306 and a first lower line 308. The two lines, 306 and 308, pass through first pinch valve 314. An example of a suitable, commercially available, three-way pinch valve for this application is Model Number 373 12-7 15, available from Angar Scientific Company, Incorporated. Pinch valve 314 closes either the upper line 306 or the lower line 308, but never both lines simultaneously. Lower line 308 provides a vent to atmospheric pressure. Upper line 306 attaches to fluid collection canister 318. Similarly, second vacuum line 136 from probe assembly 40 attaches to a second Y-connector 304 which is fluidly connected to a second upper line 310 and a second lower line 312. The first and second vacuum Y-connectors, 302 and 304, may be molded from a rigid polymer such as polycarbonate. Second upper line 310 passes through a second pinch valve 316, which is identical to the first, and to the canister 318. Second lower line 312 passes through second pinch valve 316 and vents to the atmosphere. Again, only one or the other of the two lines, 310 and 312, may be pinched closed at any time.

Still referring to fluid collection system 22 of FIG. 14, a main vacuum line 320 attaches the canister 318 to electrically powered vacuum pump 330. An example of a suitable vacuum pump for this application is available as WOB-L PISTON Series 2639 from Thomas Compressors and Vacuum Pumps, Incorporated. Main vacuum line 320 passes through regulator valve 322 to adjust electronically the vacuum pressure supplied to canister 318. An example of a commercially available regulator valve for this application is model number VSONC6S11VHQ8 from Parker Hannifin Corporation, Pneutronics Division. Pressure sensor 328 is fluidly attached to main vacuum line 320 at a sensor connection 324. The signal from pressure sensor 328 is sent to an A/D converter 396 of control unit 342. An example of a commercially available, compensated pressure sensor for this application is model number SDX15 from SenSym, Incorporated.

In FIG. 14 control unit 342 is shown to include the elements inside the drawn box, a liquid crystal display (LCD) 334, and a touchscreen 336. FIGS. 16A and 16B together form a detailed schematic of the elements of control unit 342. FIGS. 14, 16A, and 16B may be referred to concurrently for the description of the elements of control unit 342. At the heart of control unit 342 is a microprocessor 408. An example of a suitable microprocessor 408 is 40 MHz, 32-bit microprocessor, available from Motorola, Incorporated as Part Number XCF5206EFT40. Microprocessor 408 is designed to perform logic operations that may be translated into simple electromechanical actions. LCD 334 prompts and informs the operator during the operation of the biopsy device. An suitable example for LCD 334 is 640×480 color TFT-LCD display available from Sharp Electronics Corporation as part number LQ64D343. A resistive touch screen 336 covers LCD 334 for the user interface. An example of a suitable touch screen 336 is available from Dynapro Thin Film Products, Incorporated as Part Number 95638. LCD 334 is electronically connected to a touch screen controller 402 in control unit 342.

Interfacing with microprocessor 408 is an oscillator 540, an EPROM 542, and a voltage supervisor 541. Oscillator 540 is available, for example, as Part Number ASV-40.000000-PCSA (40 megahertz) from Abracon Corporation. A suitable example for EPROM 542 is Part Number AT27BV4096-15JC available from Atmel Corporation. A suitable example for voltage supervisor 541 (for a 2.93-volt supply) is available as Part Number TLC773ID from Texas Instruments, Incorporated.

Touch screen controller 402 allows control unit 342 to respond to the user's touch by interpreting touch inputs. Other more conventional devices, such as mechanical switches, may be used instead of touch screen controller 402 for controlling control unit 342. Touch screen controller 402, however, is easy to keep clean and is intuitive for the operator to use. Touch screen controller 402 comprises a microcontroller 511, an A-D converter 512, a multiplexer-demultiplexer 513, and an EEPROM 514. A suitable example for microcontroller 511 is 8-bit micro-controller Part Number 95705 from Microchip Technology, Incorporated. A suitable example for A-D converter 512 is 10-bit serial A-D converter Part Number TLV1543CDW from Texas Instruments, Incorporated. A suitable example for multiplexer-demultiplexer 513 is dual 4-to-1 line analog multiplexer-demultiplexer Part Number MC74HC4052D from Motorola, Incorporated. A suitable example for EEPROM 514 is 1K-bit serial EEPROM Part Number 93AA46SN from Microchip Technology, Incorporated.

A LCD controller 404 is provided to interface between microprocessor 408 and LCD 334. LCD controller 404 reduces the burden of microprocessor 408 by efficiently controlling display parameters such as color, shading, screen update rates, and it typically accesses the memory chips of microprocessor 408 directly. LCD controller 404 comprises a 25-megahertz oscillator 539 that is available, for example, as part number ASV-25.000000-PCSA from Abracon Corporation. LCD controller 404 also comprises an LCD/CRT controller 508 that is available, for example, as part number SED1354FOA from Seiko Epson Corporation, and a 1-meg×16-bit, 60 nanosecond, EDO DRAM 507 that is available, for example, as part number MT4LC1M16E5TG-6 from Micron Technology, Incorporated. LCD controller 404 further comprises a pair of 16-bit drivers, 509 and 510, of the non-inverting, buffer-line type, that are available, for example, as part number 74ACTQ16244SSCX from National Semiconductor Corporation.

A miniature annunciator 332 is provided with control unit 342 in order to provide the operator with audible feedback "beeps" upon each activation of an icon control on the LCD 334. An example of a suitable annunciator for this application is model number EAS-45P104S from Matshusita Electric Corporation of America (Panasonic Division). Annunciator 332 interfaces with microprocessor 408 by an oscillator 400 which converts the digital input signal from microprocessor 408 to an analog, periodic output signal, thus controlling the audio frequency of the connector 332. The volume of the sound coming from annunciator 332 is controllable, as will be described later. Referring to FIG. 16B, oscillator 400 comprises a 62 dB audio attenuator 517 that is available, for example, as Part Number LM1971M from National Semiconductor Corporation. Oscillator 400 further comprises an operational amplifier 516 that may be identical, for example, to operational amplifier 530 already described. Oscillator 515 further comprises a power audio amplifier 515 that is available, for example, as part number LM486M from National Semiconductor Corporation.

Still referring to control unit 342 shown in FIGS. 14, 16A and 16B, a first motor controller and driver 390 interfaces with translation motor 340 and with microprocessor 408. Translation motor 340 is operationally connected to second rotatable shaft 266. Controller and driver 390 converts digital input signals from microprocessor 408 into analog motor input signals for controlling motor rotational direction and speed. Closed loop digital speed control of translation motor 340 is also achieved within controller and driver 390 using feedback signals from encased rotation sensor 268 in holster 251 and rotation sensor integrated within translation motor 340. First motor controller and driver 390 comprises a first H-bridge motor driver 552 (also referred to as a first driver) and a first motor controller 523. A suitable example of a first H-bridge motor driver is available as Part Number LMD18200T from National Semiconductor Corporation. A suitable example of a motor controller is available as Part Number LM629M-8 from National Semiconductor Corporation.

Still referring to FIGS. 14, 16A, and 16B, rotation motor 338 drives first rotatable shaft 264. Rotation motor 338 interfaces with microprocessor 408 through second controller and driver 406 which comprises a second H-bridge motor driver 551 (also referred to as a second driver) and a second motor controller 522. Second H-bridge motor driver 551 may be identical to first H-bridge motor driver 552, already described. Second motor controller 522 may be identical to first motor controller 523, already described. Microprocessor 408 via second controller and driver 406 continually calculates and updates the rotational positions of cutter 96, as well as the rotational speed and acceleration, using feedback signals from the rotation sensor integrated within rotation motor 338.

Still referring to control unit 342 shown in FIGS. 14, 16A, and 16B, a serial controller 380 is electronically connected to switchboard 274 by ribbon cable 270 and control cord 265. Ribbon cable 270 is contained within holster 251. Control cord 265 runs along, and may be attached to, first rotatable shaft 264 and second rotatable shaft 266. Serial controller 380 coordinates information exchange across the serial communication link between switchboard 274 and microprocessor 408. An optional card reader 382 may be provided in control unit 342 for reading data from memory card in order to facilitate future software upgrades and servicing. A serial port 384 is provided for the bi-directional data exchange in a serial transmission mode, again to facilitate future software upgrades and servicing. Serial controller 380 includes a quad differential line receiver 524 that is available, for example, as Part Number DS90C032TM from National Semiconductor Corporation. Serial controller 380 further includes an ESD (electrostatic discharge) over-voltage protection array 525 that is available, for example, as Part Number SP723AB from Harris Semiconductor Products.

A first PWM (pulse width modulation) driver 386 interfaces first pinch valve 314 with microprocessor 408. First PWM driver 386 converts a digital input signal from microprocessor 408 to an analog output signal having a wave of fixed frequency and amplitude, but varying duty cycle. To drive the solenoid in pinch valve 314, PWM driver 386 is used when the duty cycle is high to initially move the solenoid. Once pinch valve 314 is actuated, the duty cycle is reduced to a level, which maintains valve position, thus minimizing power requirements. A second PWM driver 388 similarly interfaces a second pinch valve 316 with microprocessor 408. A suitable example for both first PWM driver 386 and second PWM driver 388 is FET (60 volt, 3.5 amp, 0.10 ohm, N-channel dual) Part Number NDS9945 available from Fairchild Semiconductor Corporation.

Referring to FIG. 16B, a first EPLD (Erasable Programmable Logic Device) 521 interfaces with LCD controller 404, PWM driver 388, PWM driver 386, an FET 554, oscillator 400, a first 8 MHz. oscillator 538, serial controller 380, and microprocessor 408 (via the path represented by the encircled "A"). A suitable example for first EPLD 521 is available as Part Number EPM7256ATC144-7 from Altera Corporation. FET 554 may be identical, for example, to FET 556 of second PWM driver 388. First oscillator 538 is available, for example, as Part Number ASL-8.000000-PCSA from Abracon Corporation.

A second EPLD 520 interfaces microprocessor 408 with serial port 384, first controller and driver 390, second controller and driver 406, touch screen controller 402, RAM 392, flash memory 398, and oscillator 540. EPLD 520 is capable of operating at 166.7 megahertz and is available, for example, as Part Number EPM7256ATC144-7 from Altera Corporation.

A third PWM driver 394 interfaces with regulator valve 322 and A/D converter 396. PWM driver 394 comprises a voltage reference device 526 comprising a first operational amplifier and a voltage reference. PWM driver 394 further comprises a second operational amplifier 527, a third operational amplifier 528, a fourth operational amplifier 529, a fifth operational amplifier 530, a sixth operational amplifier 531, and a seventh operational amplifier 532. The operational amplifier in voltage reference device 526, and operational amplifiers 527, 528, 529, 530, 531, and 532 are more descriptively referred to as "Quad Rail-to-Rail Operational Amplifiers". A suitable example for each is available as Part Number LMC6484IM from the National Semiconductor Corporation. PWM driver 394 further comprises a first FET (Field Effect Transistor) 553. A suitable example of FET 553 is available as Part Number NDS9945 (60 volt, 3.5 amp, 0.10 ohm, N-channel dual) from Fairchild Semiconductor Corporation.

A RAM (Random Access Memory) memory device 392 (also referred to as a temporary memory device) is provided with microprocessor 408, and inherently loses stored data when power is removed. A flash memory device 398 (also referred to as a non-volatile memory device), on the other hand, is provided with microprocessor 408 to store data even without power, but it has slower access time than RAM memory device 392. RAM memory device 392 comprises four EDO DRAM devices, 547, 548, 549, and 550. These devices may be identical and a suitable example of each is available as Part Number MT4LC1M16E5TG-6 from Micron Technology, Incorporated. Flash memory device 398 comprises four RAM devices 543, 544, 545, and 546 which may be identical and a suitable example of each is available as Part Number AM29LV800BT-70REC from Advanced Micro Devices, Incorporated. The combination of the RAM memory device (temporary memory device) 392, the flash memory device (non-volatile memory device) 398, and the microprocessor 408 is sometimes referred to simply as a computing device. The computing device may also include the first controller 523 and the second controller 522 in an alternate embodiment.

Serial port 384 comprises a dual, universal, asynchronous receiver/transmitter 533 available, for example, as part number ST16C2552CJ44 from Exar Corporation. Serial port 384 further comprises a first driver-receiver 534 and a second driver-receiver 535, each more descriptively called a "TIA/EIA-232, 3×5 driver-receiver" and available, for example, as Part Number DS14C335MSA from National Semiconductor Corporation. Serial port 384 further includes a first transient suppressor 536 and a second transient suppressor 537, each a bi-directional, 24 volt, 300 watt unit available, for example, as Part Number SMDA24C-8 from General Semiconductor, Incorporated.

Location for an optional card reader 382 interfacing with microprocessor 408 is also shown in FIG. 16A. Card reader 382 may be used in future embodiments of the biopsy device to program control unit 342 with alternate values, for example, of the desired translation and rotation speeds of the cutter 96.

An A/D converter 396 converts voltage signals from pressure sensor 328 into digital signals which are transmitted to microprocessor 408, and used by microprocessor 408 to maintain a desired vacuum pressure in fluid collection system 22. A suitable example of A/D converter 396 is ADC-DAC, 8-bit, 12C bus interface available as Part Number PCF8591AT from Philips Electronics N.V.

The biopsy device is provided with a conventional, 48-volt DC power supply used in combination with standard DC-to-DC converters and electrical voltage regulators in order to supply reduced voltages to the components of control unit 342.

The microprocessor 408 may be used to monitor the output value of second controller and driver 406 PID filter such that if the output of it exceeds a predefined maximum value, the translational speed of cutter 96 is reduced a set amount by sending an updated speed command to first controller and driver 390. This closed-loop system insures that the desired cutter rotational speed is maintained by decreasing the translational speed of cutter 96. This automatic adjustment to cutter translational speed occurs when cutter rotational resistance becomes abnormally high. Cutter rotational resistance is the combination of cutting resistance (when the cutter 96 encounters obstructions, very dense tissue, or calcified lesions, for example) and mechanical resistance (when the operator, for example, manipulates piercer 70 into tissue with enough force to place a significant bending moment on piercer 70 so that cutter 96 binds inside piercer lumen 80.) Rather than attempting to maintain cutter translational speed by ramping up cutter rotational speed, the cutter translational speed is decreased in order to reduce the cutter rotational resistance. In one embodiment of the present invention, this is accomplished in the following manner. While in the sampling mode and with cutter 96 advancing toward the third position (proximal to port 78), when cutter 96 reaches a predetermined translational position, microprocessor 408 sends a signal to second controller and driver 406 to initiate cutter rotation. The rotational speed of cutter 96 follows a predefined speed profile which insures that the cutter rotational speed is at a predetermined Q (also referred to as predetermined rotational speed) revolutions per minute (rpm) when cutter 96 reaches the third position. When cutter 96 reaches the third position, microprocessor 408 sends a signal to first controller and driver 390 to advance cutter 96 at a predetermined translation speed T (also referred to as a third, predetermined translation speed) inches per second (in/sec). Cutter 96 then progresses through port 78 at predetermined translation speed T in/sec while rotating at velocity Q rpm. While advancing through port 78, cutter 96 rotational speed is monitored by second controller and driver 406, using signals from the rotation sensor integrated within rotation motor 338. If the rotational speed is greater than Q rpm, electrical current to translation motor 340 is increased. If the cutter rotational speed is less than Q rpm, electrical current to translation motor 340 is decreased.

If it is desired to control the speed of either translation motor 340 or rotation motor 338 in response to increased cutter rotation resistance, such as in a further embodiment of the present invention, one way to do so is to generate an error signal based on the difference between the desired speed (translation or rotation, depending on which motor is controlled) and the actual speed. The error signal is then input into a proportional, integral, and derivative (PID) digital filter, which is part of the respective controller and driver, either first controller and driver 390, or second controller and driver 406. The sum of these three terms is used to generate the pulse width modulation (PWM) signal. First and second controller and driver, 390 and 406, each generate the error signal and the PWM signal. A PWM signal is input to first controller and driver 390 to generate an analog output signal to drive translation motor 340. Similarly, a PWM signal is input to the second controller and driver 406 to generate an analog output signal to drive rotation motor 338.

Figure 15:
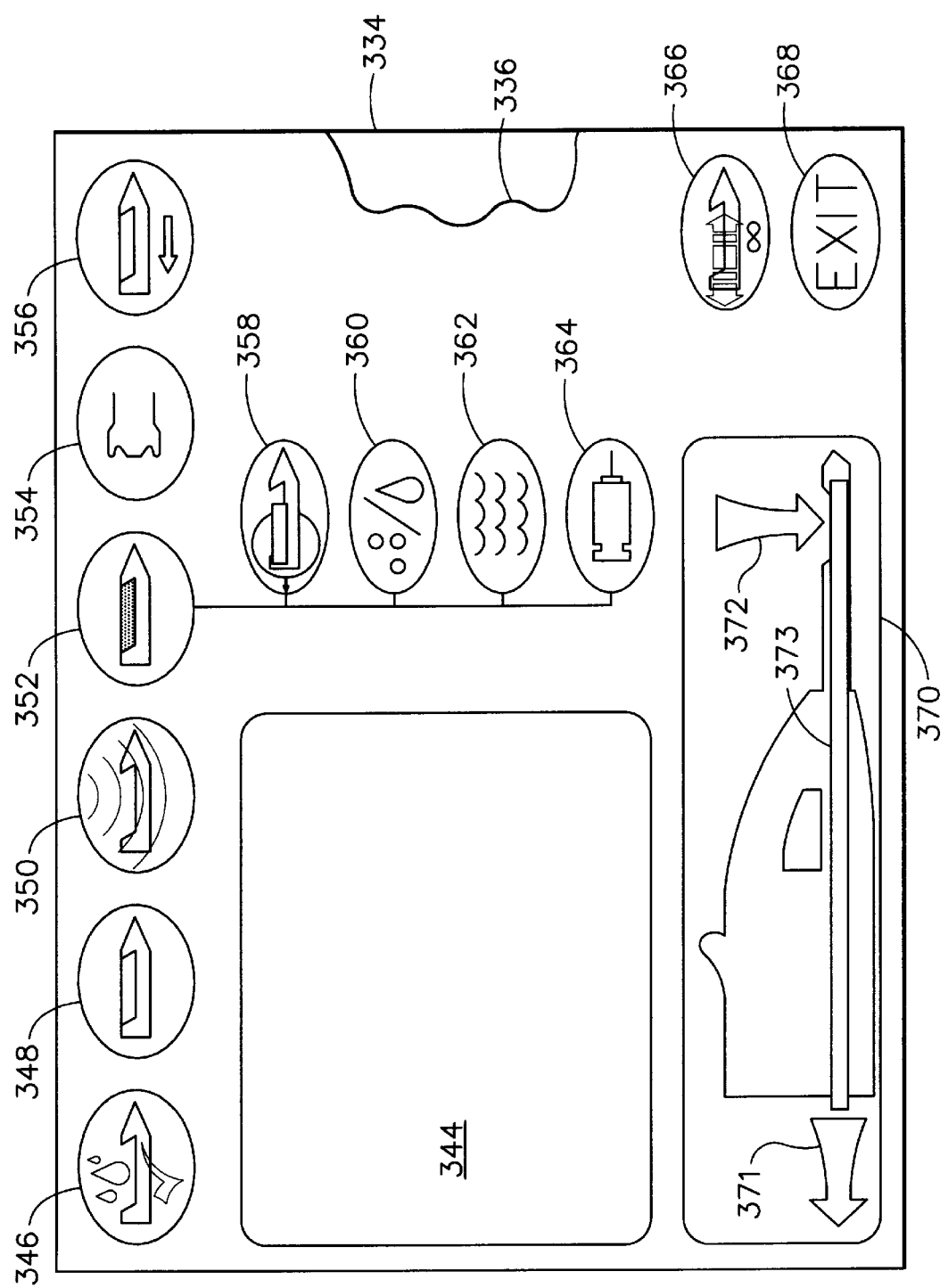
FIG. 15 is an enlarged diagram of an LCD display illustrated in FIG. 14.

Next is described the operator interface for the biopsy device according to the present invention. FIG. 15 is an enlarged view of LCD 334 having a display area 344, and touch screen 336, both of which are part of control unit 342 of FIG. 14. In one embodiment of the present invention, twelve separate operating modes are available to a user. A control switch for each operating mode is displayed graphically on LCD 334 in the form of icons, 346, 348, 350, 352, 354, 356, 358, 360, 362, 364, 366, and 368. The user may initiate a particular operation by pressing touch screen 336 in the region of the appropriate icon at the appropriate time during the surgical procedure to electronically control the operation of the biopsy device.

Each mode of operation is utilized for a particular portion of the general biopsy procedure. The "Prime" mode of operation is selected when the operator is preparing the instrument for use. When an operator activates the "Prime" mode of operation by, for example, touching the LCD 334 in the region of icon 346, display area 344 indicates the status as being "Prime Mode". Cutter 96 then translates to the third position just proximal to port 78. Once cutter 96 is in the third position, display area 344 instructs the operator to apply saline to port 78 and to depress vacuum switch 150 as needed to draw saline into piercer 70 and through probe assembly 40. The operator may observe the flow of saline through window 58. Finally, first pinch valve 314 and second pinch valve 316 are each set to respond to vacuum switch 150.

The "Insert" mode of operation is next selected when the operator is preparing to insert the piercer into tissue. When an operator activates the "Insert" mode of operation by, for example, touching LCD 334 in the region of Icon 348, display area 344 indicates the status as being "Insert Mode". Cutter 96 then translates to the fourth position, just distal to port 78. Once cutter 96 translates to the fourth position, the display indicates that the instrument is ready to insert.

The "Verify" mode of operation is selected when the operator wants to verify whether or not cutter 96 is at the fourth position. When an operator activates the "Verify" mode of operation by, for example, touching LCD 334 in the region of Icon 350, display area 344 indicates the status as being "Verify Mode". If cutter 96 is not at the fourth position, translation motor 340 is set to respond to forward switch 146 on handpiece 20. Then display area 344 instructs the operator to close port 78 by pressing forward switch 146 on handpiece 20. When the operator presses forward switch 146, cutter 96 translates to the fourth position. Translation motor 340 is then set to respond to reverse switch 148 on handpiece 20. If cutter 96 is already at the fourth position when the "Verify" mode is selected, then second motor 340 is set to respond to reverse switch 148. Then display area 344 instructs the operator to open port 78 by pressing reverse switch 148 on handpiece 20. When the operator presses reverse switch 148, cutter 96 translates to the third position just proximal to port 78. Then translation motor 340 is set to respond to forward switch 146.

The "Sample" mode of operation is selected when the operator desires to extract a portion of tissue from the surgical patient. When the operator activates the "Sample" mode of operation by, for example, touching LCD 334 in the region of icon 352, display area 344 indicates the status as being " "Sample Mode". Cutter 96 then translates to the third position, which is just proximal to port 78. Then translation motor 340 is set to respond to forward switch 146. Once cutter 96 is in the third position, display area 344 instructs the operator to take a tissue sample by pressing forward switch 146 on handpiece 20. When forward switch 146 is pressed, first pinch valve 314 and second pinch valve 316 are opened, and rotation motor 338 is activated to rotate cutter 96 at the appropriate speed. Then cutter 96 translates to the fourth position, severing the tissue portion prolapsed into port 78 as cutter 96 moves distally. During translation to the fourth position, the operator may abort the sampling stroke, prior to cutter 96 reaching the midpoint of port 78, by pressing any one of the forward, reverse, or vacuum switches, 146, 147, or 150 respectively, on handpiece 20. At this point cutter 96 translation is halted and display area 344 instructs the operator to either continue sampling by pressing forward switch 146 or reverse switch 148 to return to the first, fully retracted position. Once cutter 96 reaches the fourth position, rotation motor 338 is deactivated and cutter 96 stops rotating. Then first pinch valve 314 is activated to close first upper line 306. Next display area 344 instructs an operator to retrieve a tissue sample by pressing reverse switch 148 on handpiece 20. Translation motor 340 is set to respond to reverse button 148 on handpiece 20. When the operator presses reverse switch 148, cutter 96 translates to the first, fully retracted position, just distal to sampling surface 64. Then second pinch valve 316 is activated to close the vacuum for tissue remover 132. A "smart-vacuum" is also activated and a plurality of vacuum pulses (0.5 seconds on and 0.5 seconds off) are supplied to second vacuum tube 136. A detailed description of the "smart vacuum" is provided in U.S. patent application Ser. No. 08/878,468 filed on Jun. 18, 1997 and hereby incorporated herein by reference. Display area 344 then instructs the operator to remove the tissue sample 200. If there was no sample extracted, that is, the severed tissue sample remained at the distal end of piercer 70 and was not deposited onto tissue sample surface 64, the operator is instructed to select "Dry Tap". The operator is also instructed to select "Remove Air/Blood" if required to remove excessive fluids in the patient and in probe assembly 40. The operator is finally instructed to press forward switch 146 on handpiece 20 to extract the next sample. Next, translation motor 340 is set to respond to forward switch 146 on handpiece 20. When forward switch 146 is pressed by the operator, the "smart-vacuum" is stopped and first and second pinch valves, 314 and 316, are activated to open. Rotation motor 338 is activated to rotate cutter 96, which then translates to the fourth, fully distal position. Then cutter 96 rotation is stopped and first pinch valve 314 is closed to stop the vacuum to vacuum pressure chamber tube 76 supplied by first vacuum tube 94.

The "Mark" mode of operation is selected when the operator desires to implant a metallic marker within the surgical patient at the location from which the tissue sample 200 was extracted. When the operator activates the "Mark" mode of operation by, for example, touching LCD 334 in the region of icon 354, display area 344 indicates the status as being "Marker Mode" and also prompts the operator to select "Dry Tap" if required. Then the operator is instructed to press vacuum switch 150 on handpiece 20 to activate the "Mark" mode. A marking instrument which may be used in combination with the present invention for marking tissue is commercially available under the trade name MICROMARK from Ethicon Endo-Surgery, Inc., Cincinnati, Ohio. A complete description of the MICROMARK applier and clip, and the method of its use, is included in U.S. patent application Ser. No. 09/105,757 and Ser. No. 09/105,570, both filed on Jun. 26, 1998, and which are hereby incorporated herein by reference. When the operator presses vacuum switch 150, cutter 96 translates to the first position just proximal to tissue sampling area 64. Display area 344 then instructs the operator to insert the MICROMARK instrument, to press vacuum switch 150 on handpiece 20 when ready to deploy, and to deploy the marker. Then when vacuum switch 150 is pressed, first pinch valve 314 is activated to the open position for five seconds to supply vacuum to the port 78 through vacuum chamber 76. Next display area 344 instructs the operator to reposition the MICROMARK instrument if marker deployment was not complete, to press vacuum switch 150 on the handpiece 20 when ready to deploy the marker, to deploy the marker, and if the marker deployment is complete, to remove the MICROMARK instrument.

The "Remove" mode of operation is selected when the operator is ready to remove piercer 70 from within the tissue of the surgical patient. When the operator activates the "Remove" mode of operation by, for example, touching LCD 334 in the region of icon 356, display area 344 indicates the status as being "Remove Mode". Cutter 96 translates to the fourth, fully distal position and closes port 78. Display area 344 instructs the operator that the instrument is ready to remove.

The "Remove Air/Blood" mode of operation is selected when the operator desires to remove any fluids present near the distal end of piercer 78 and within probe assembly 40. When the operator activates the "Remove Air/Blood" mode of operation by, for example, pressing LCD 334 in the region of icon 360, Display area 344 indicates the status as being "Remove Air/Blood Mode". Cutter 96 then translates to the third position just proximal to the port 78. First pinch valve 314 and second pinch valve 316 are each set to respond to vacuum switch 150 on handpiece 20. Display area 344 then instructs the operator to remove the air/blood by pressing vacuum switch 150 on handpiece 20. When vacuum switch 150 is pressed, first pinch valve 314 and second pinch valve 316 are activated to open for five seconds. When they are closed, cutter 96 then translates to the first, fully retracted position just proximal to tissue sampling surface 64. Then the "Remove Air/Blood" mode is automatically exited and the previous mode selected is automatically reset.

The "Dry Tap" mode of operation is selected for when the operator had attempted to extract a tissue portion from the surgical patient using the "Sample" mode of operation, but a tissue sample 200 was not deposited onto tissue sample surface 64. This may occur when the tissue sample 200 is properly severed from the surgical patient, but remained in the distal end of piercer 78. When the operator activates the "Dry Tap" mode of operation by, for example, touching LCD 334 in the region of icon 358, display area 344 indicates the status as being "Dry Tap Mode". Cutter 96 then translates to the third position just proximal to port 78. Then second pinch valve 316 is activated to open for 0.5 seconds and to close for 0.5 seconds three times in order to pulse the vacuum supplied to tissue remover 132 through second vacuum tube 136. Cutter 96 then translates to the first, fully retracted position just distal to tissue sampling surface 64. The "Dry Tap" mode of operation is then exited and the previously selected mode of operation is automatically selected.

The "Flush" mode of operation is selected when the operator desires to clear any obstructions (tissue fragments, etc.) on the distal end of tissue remover 132 to enable the passage of fluids through it. When an operator activates the "Flush" mode of operation by, for example, touching LCD 334 in the region of icon 362, Display area 344 indicates the status as being "Flush Mode". Cutter 96 then translates to the first, fully retracted position, thus exposing the distal end of tissue remover 132. Then control unit 342 is set to respond to vacuum switch 150, which when pressed by the operator, causes the "Flush" mode of operation to be exited and the previously selected mode of operation to be automatically reset. Before pressing vacuum switch 150, however, the operator may temporarily disconnect second connector 304, inject fluid such as saline into second vacuum tube 136 using a syringe, and reconnect second connector 304.

The "Inject" mode of operation is selected when the operator desires to inject a fluid, such as a local anesthetic, into the tissue surrounding the distal end of piercer 78. When the operator activates the "Inject" mode of operation by, for example, touching LCD 334 in the region of icon 364, Display area 344 indicates the status as being "Inject Mode". Cutter 96 then translates to the second position just proximal to port 78. Then control unit 342 is set to respond to vacuum switch 150 on the handpiece 20. Next LCD display instructs the operator to inject the fluid into second vacuum tube 136, and to press vacuum switch 150 again once the injection is complete. When the operator has completed the injection into second vacuum tube 136, reconnected it to fluid collection system 22, and pressed vacuum switch 150, cutter 96 translates to the first, fully retracted position. At that point, the "Inject" mode of operation is exited, and the previously selected mode of operation is automatically reset.

The "Manual" mode of operation is selected when the operator desires to perform cutter positioning and/or vacuum functions manually. When the operator activates the "Manual" mode of operation by, for example, touching LCD 334 in the region of icon 366, Display area 344 indicates the status as being "Manual Mode." In this mode, translation motor 340 is set to respond to forward switch 146 and reverse switch 148 for the duration of switch depression. The operator at any point between the first, fully retracted position, and the fourth, fully distal position may halt translation of cutter 96. Additionally, first pinch valve 314 and second pinch valve 316 are each set to respond to vacuum switch 150.

An alternative way of selecting the operating mode is available to the operator. By a rapid double clicking of vacuum switch 150 on handpiece 20, the unit is placed in a "Scroll" mode of operation. Display area 344 instructs the operator to press forward switch 146 or reverse switch 148 to move to the desired operational mode. Upon reaching the selected mode, it is actuated by pressing vacuum switch 150. This way of selecting the operating mode is especially useful to an operator who does not have an assistant (with clean hands) to use touch screen 336 while the operator is manipulating the imaging device and handpiece 20.

Each time one of the available operating modes is selected, Display area 344 provides written and graphic information to prompt the user as to the correct usage of the instrument and the next operational steps. A mode indicator display 370 includes a representation of the probe assembly 40 showing the instantaneous position of cutter 96, referred to as a cutter position indicator 373. Mode indicator display 370 also shows activation of a front vacuum indicator 372 (corresponding with first vacuum tube 94), and activation of a rear vacuum indicator 371 (corresponding with the second vacuum tube 136).

FIGS. 17A, 17B, 17C, and 17D illustrate a flow diagram of a first control method embodiment according to the present invention, wherein the cutter 96 has four distinct positions. FIGS. 17A, 17B, 17C, and 17E illustrate a flow diagram of a second control method embodiment according to the present invention, wherein the cutter 96 also has four distinct positions. The steps of the control method are represented in the flow chart. Even though each box may represent more than one step, or may only be part of a step, each box is referred to simply as a step. Progression of the steps occurs generally in the direction of the arrows connecting the boxes. The first and second control method embodiments may be used with any of the biopsy instrument embodiments shown in FIGS. 5, 10, and 13. In the following description of the first and second control method embodiments, however, the biopsy instrument embodiment shown in FIG. 13, also shown in FIG. 14, will be referred to.

Figure 17A:
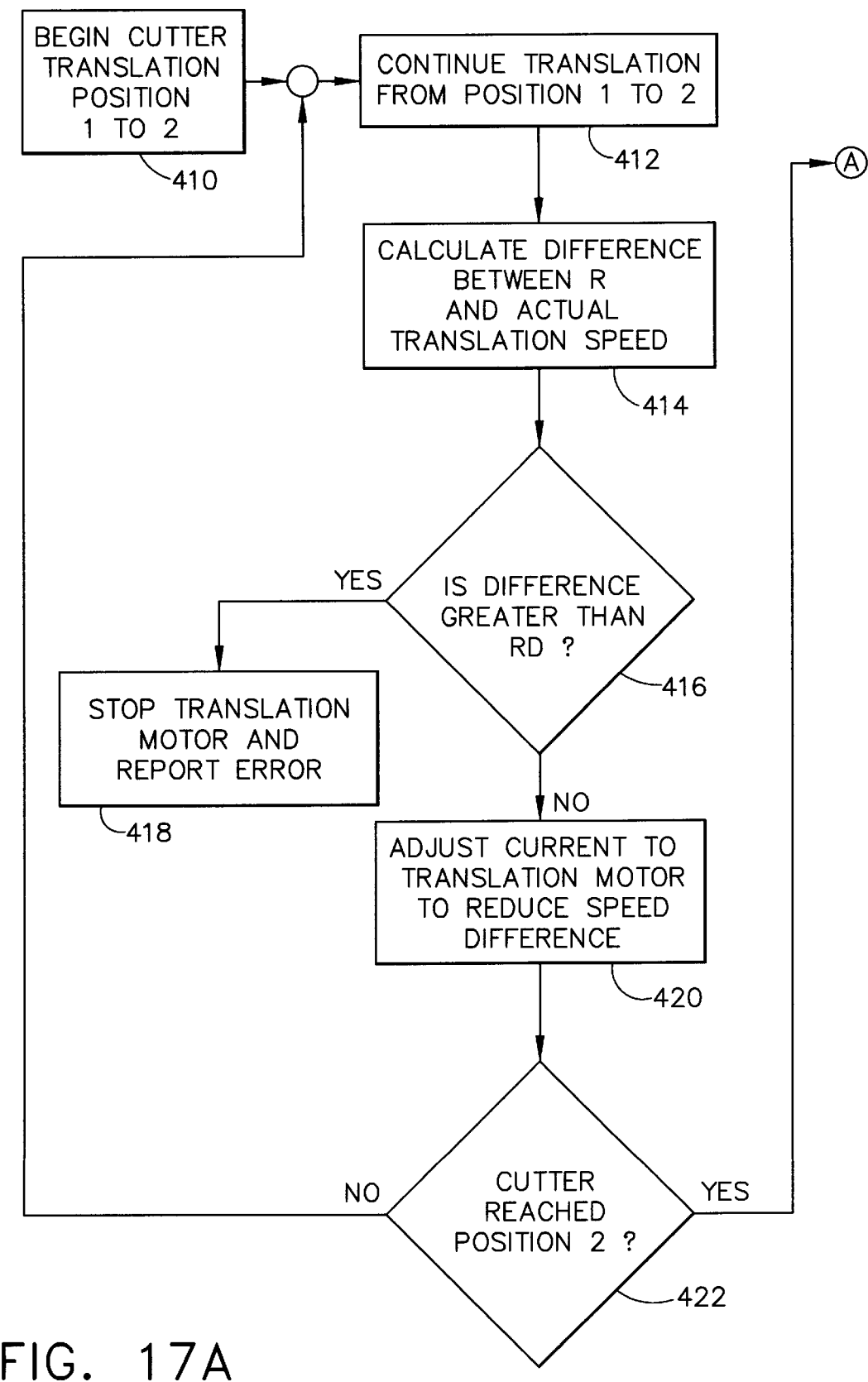
FIG. 17A is a first portion of a flow chart pertaining to a first embodiment and a second embodiment of a control method for the operation of the cutter, showing the control unit logic for when the cutter translates from the first position to the second position.
Figure 17B:
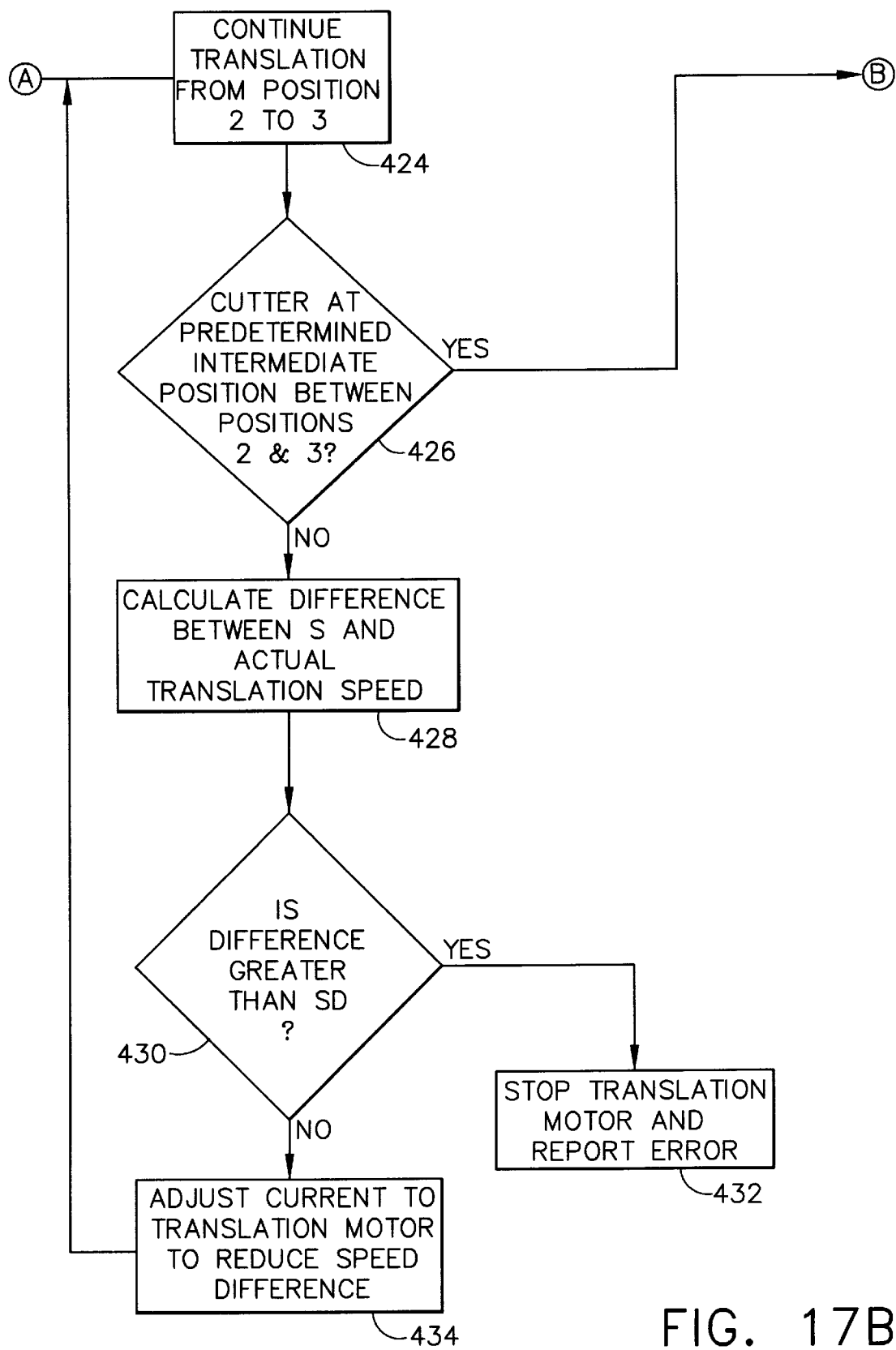
FIG. 17B is a second portion of a flow chart pertaining to the first embodiment and the second embodiment of the control method for the operation of the cutter, showing the control unit logic for when the cutter translates from the second position to the third position.
Figure 17C:
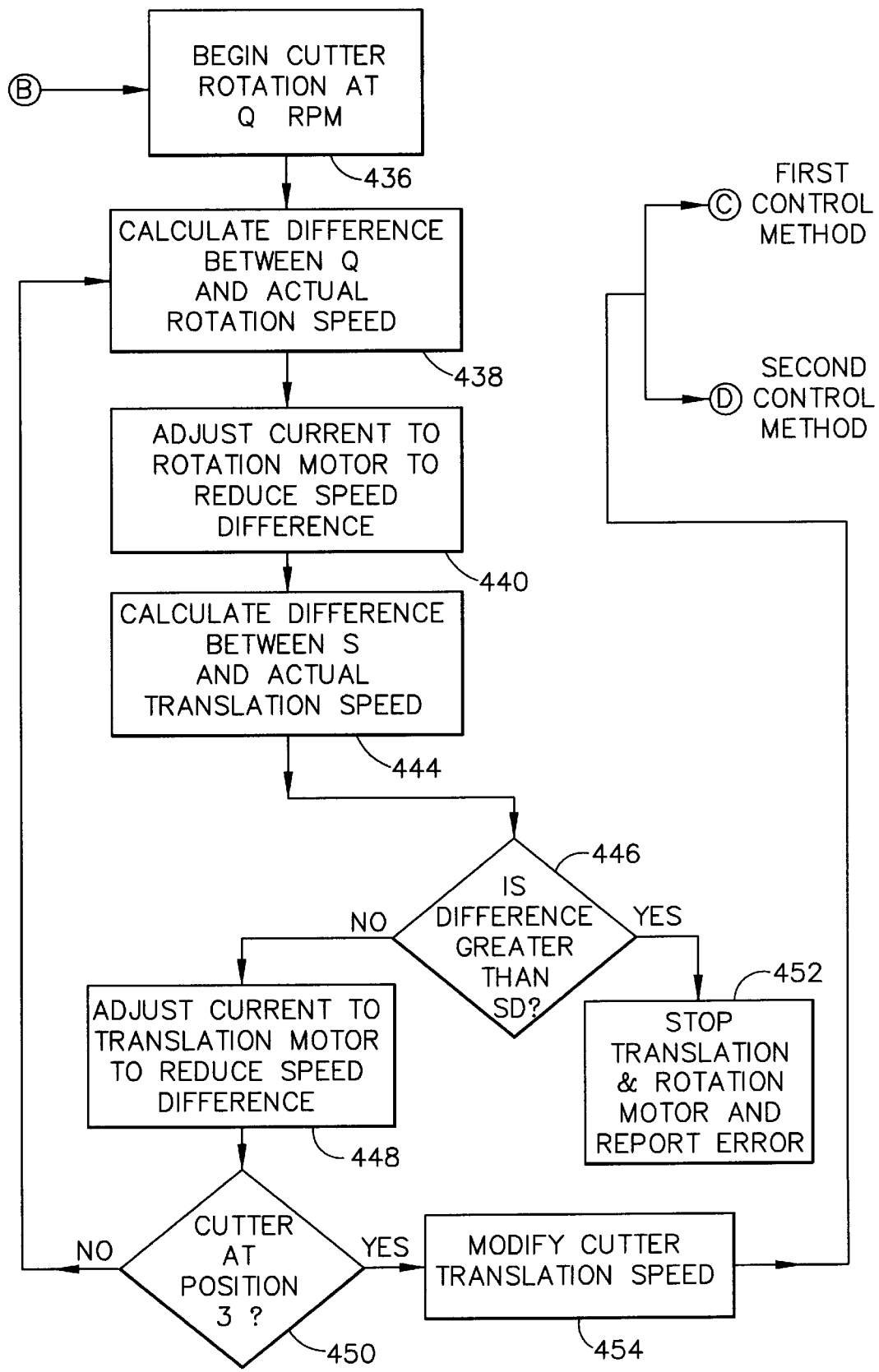
FIG. 17C is a third portion of a flow chart pertaining to the first embodiment and the second embodiment of the control method for the operation of the cutter, showing additional control unit logic for when the cutter translates from the second position to the third position.

The steps for the first and second control method embodiments are identical for FIGS. 17A, 17B, and 17C. Please see FIG. 16 for references to elements of control unit 342. Referring first to FIG. 17A, step 410 represents the beginning of the control method. When either the "manual" or "sample" modes of operation are activated, the serial communication loop is completed through microprocessor 408 and EPLD 520 to receive the switch interface data for the initiation of controller 523 to enable H-bridge motor driver 552 to send the appropriate current to translation motor 340. Cutter 96 begins to move distally from the first position, but does not rotate. At step 412, cutter 96 continues to translate from position one to position two. At step 414, a signal is read from the encoder (also referred to as the first sensor) of translation motor 340 and compared with a first, predetermined translation speed R programmed in controller 523. The value of R may vary for different embodiments, but a preferred value for R is approximately in the range of 0.67 inches/second. A difference between R and the actual translation speed of the cutter 96 is calculated and in step 416, the difference is compared to a programmed value called RD (also referred to as a first predetermined differential translation speed), which represents an allowable differential for the value R. A preferred value for RD is approximately in the range of 0.02 inches/second. If the calculated difference between R and the actual speed is greater than RD, then current to translation motor 340 is stopped (step 418) and the error is reported on the display area 344. If the translation speed difference is less than RD, then the current to translation motor 340 is adjusted to reduce the translation speed difference, as represented by step 420. The cutter 96 continuously adjusts translation speed in this way until cutter 96 reaches position two, as shown in step 422. The number of translation motor 340 rotations are counted by rotation sensor 268, so that the number of screw rotations of screw 114 (see FIG. 9) can be determined, thus providing the position of carriage 124 (see FIG. 9), and finally the position of cutter 96. Correction for twisting of rotatable shaft 266 is calculated at this point of the control method by using the signals from both rotation sensor 268 and the encoder integral to translation motor 340.

The control method next progresses to step 424 of FIG. 17B for continuing the translation of the cutter 96 from position two to position three. Next in step 426 if cutter 96 has reached a predetermined intermediate position between two and three, then the control method progresses to step 428. The location of the predetermined intermediate position is based on the actual translation speed and predetermined cutter rotation speed Q. This is to allow a sufficient amount of time for cutter 96 to accelerate from zero to the predetermined rotation speed Q before cutter 96 has reached position 3, where cutting of tissue begins. The actual translation speed is compared to a second, predetermined translation speed S, which is programmed into the controller 523. The difference is calculated in step 428 and compared in step 430 to a value SD, the allowable differential, (also referred to as a second, differential translation speed) which is programmed in controller 523. A preferred value for SD is approximately in the range of 0.02 inches/second. Value S may vary for different embodiments, but a preferred value of predetermined translation speed S is approximately in the range of 1.45 inches/second. The second predetermined translation speed S is much higher than first predetermined translation speed R because the distance traversed by the cutter 96 is much greater between positions 2 and 3 than between positions 1 and 2. Reducing the time to operate the device during the sample mode is important in reducing the overall duration of the surgical procedure because several samples may be taken from the tissue of the patient. In addition, between positions two and three, sharp distal end 72 (of cutter 96) is protected by piercer 70. Sharp distal end 72, however, is exposed between positions one and two, making it advantageous to move slower between positions one and two. In step 430, if the calculated difference between S and actual speed is greater than SD, than controller 523 signals H-bridge motor driver 552 to stop the current to translation motor 340 in step 432, thus stopping the advancement of cutter 96. If the difference between S and the actual speed is not greater than SD, then the current is adjusted to reduce the speed difference, as indicated in step 434. The control method next progresses to step 424 to continue the translation of cutter 96 from position two to three. For step 434, if cutter 96 has not reached position three, the adjustments to translation motor speed continue as already described. If cutter 96 has reached position three, then the control method progresses to step 436 of FIG. 17C.

Now referring to FIG. 17C, cutter 96 is still translating from position two to position three. At step 436 microprocessor 408 and EPLD 520 initiate second controller 522 to enable second H-bridge driver 551 to supply the appropriate current to rotation motor 338 to rotate at a predetermined rotation speed of Q. The value of Q may vary for different embodiments, but a preferred value for Q is approximately 1350 revolutions per minute (rpm). It has been found through experimentation that at this speed, the tissue is normally cut cleanly and without tearing, resulting in a good core tissue sample. In step 438 the difference between predetermined rotation speed Q and the actual rotation speed is calculated in controller 522 using the signal from the integral encoder of rotation motor 338. Then in step 440 the current to rotation motor 338 is adjusted to reduce the rotation speed difference. As before, the actual translation speed is compared to predetermined translation speed S, which is programmed into controller 523. The difference is calculated in step 444 and compared in step 446 to a value SD, the allowable differential translation speed, also referred to as a second, predetermined differential translation speed, which is programmed in controller 523. In step 452, if the calculated difference between S and actual speed is greater than SD, than controller 523 signals H-bridge motor driver 552 to stop the current to translation motor 340 and rotation motor 338, thus stopping the advancement and rotation of cutter 96. If the difference between S and the actual speed is not greater than SD, then the current to translation motor 340 is adjusted to reduce the speed difference, as indicated in step 448. In step 450, if cutter 96 has not reached position three, then control goes back to step 438. If cutter 96 has reached position three, then the control method proceeds to step 454, where first controller 523 initiates first H-bridge driver 552 to modify the current to translation motor 340 to change the cutter translation speed to a new commanded translation speed. A preferred initial value for the commanded translation speed is approximately in the range of 0.28 inches/second. It was found through experimentation that this value for initial commanded translation speed provides a clean core tissue sample. The initial commanded translation speed is slower than the speeds during the other segments of the cutter 96 journey because a slower speed is desired for severing tissue between positions 3 and 4 along the length of the port 78. The subsequently commanded translation speeds may be less due to increased cutter rotational resistance, as is described next. After reaching step 454, the control method may continue either as an embodiment identified as "First Control Method" (encircled letter "C") or as a further embodiment identified as "Second Control Method" (encircled letter "D"). The control method of the present invention is not limited to these two embodiments; they are provided as examples of the method according to the present invention.

Figure 17D:
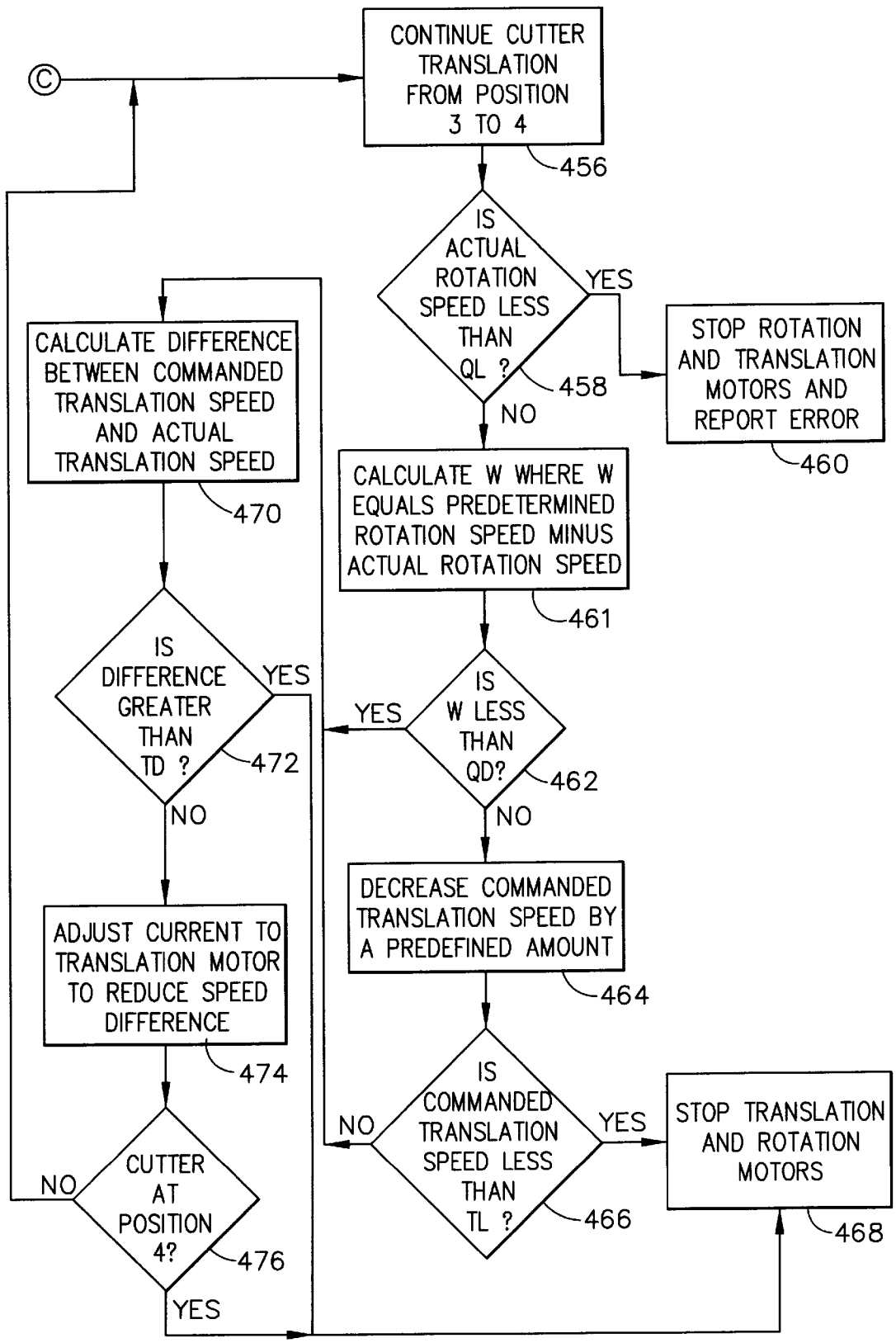
FIG. 17D is a fourth portion of a flow chart pertaining specifically to the first control method embodiment for the operation of the cutter, showing the control unit logic for when the cutter translates from the third position to the fourth position.

Now referring to FIG. 17D which describes the last portion of the first control method embodiment, in step 456 cutter 96 continues to translate distally from position three towards position four. In step 458, the actual rotation speed of cutter 96 is compared to a lowest allowable rotation speed QL (also referred to as a predetermined minimal rotation speed). A preferred value for QL is about 1200 rpm, although this value may vary. The integral encoder of rotation motor 338 sends a signal to be compared with the programmed value for QL in second controller 522. If the actual rotation speed is less than QL, then both rotation motor 338 and translation motor 340 are stopped (step 460) and the error is reported on display area 344. If rotation speed is greater than QL, than the control method proceeds to step 461 to calculate W, where W equals predetermined rotation speed minus actual rotation speed. In step 462, if the predetermined rotation speed minus the actual rotation speed is less than QD, a predetermined differential rotation speed, then the control method proceeds to step 470. A preferred value for QD is approximately in the range of 200 rpm. If W is not less than QD, the commanded translational speed is decreased by a predefined amount as specified in step 464. An approximate value for the predefined amount is in the range of 0.06 in/sec. Then the control method progresses to step 466. If commanded translation speed is less than a predetermined minimal translation speed, TL, then the control method proceeds to step 468. An approximate value for TL is in the range of 0.06 in/sec. If not, then the control method proceeds to step 470 where, as in previous steps, the commanded translation speed is compared to the actual translation speed as measured by the integral encoder on translation motor 340. If the calculated difference in step 472 is greater than an allowable TD (also referred to as a third, predetermined differential translation speed) in step 450, then current to translation motor 340 and rotation motor 338 is stopped and the error is reported in step 468. If the difference is not greater than TD, then the current to translation motor 340 is adjusted in step 474 to reduce the speed difference in the same manner as before. A preferred value of TD is approximately in the range of 0.01 inches/second although this value may vary in other embodiments. In step 476, if cutter 96 has reached position four (the most distal position of the cutter) then rotation and translation motors, 338 and 340 respectively, are stopped (step 468), and cutter 96 stops immediately, regardless of the translational position. If cutter 96 has not reached position four, then the control method goes back to step 456 and the adjustments to translation and rotation speeds continue as before.

Figure 17E:
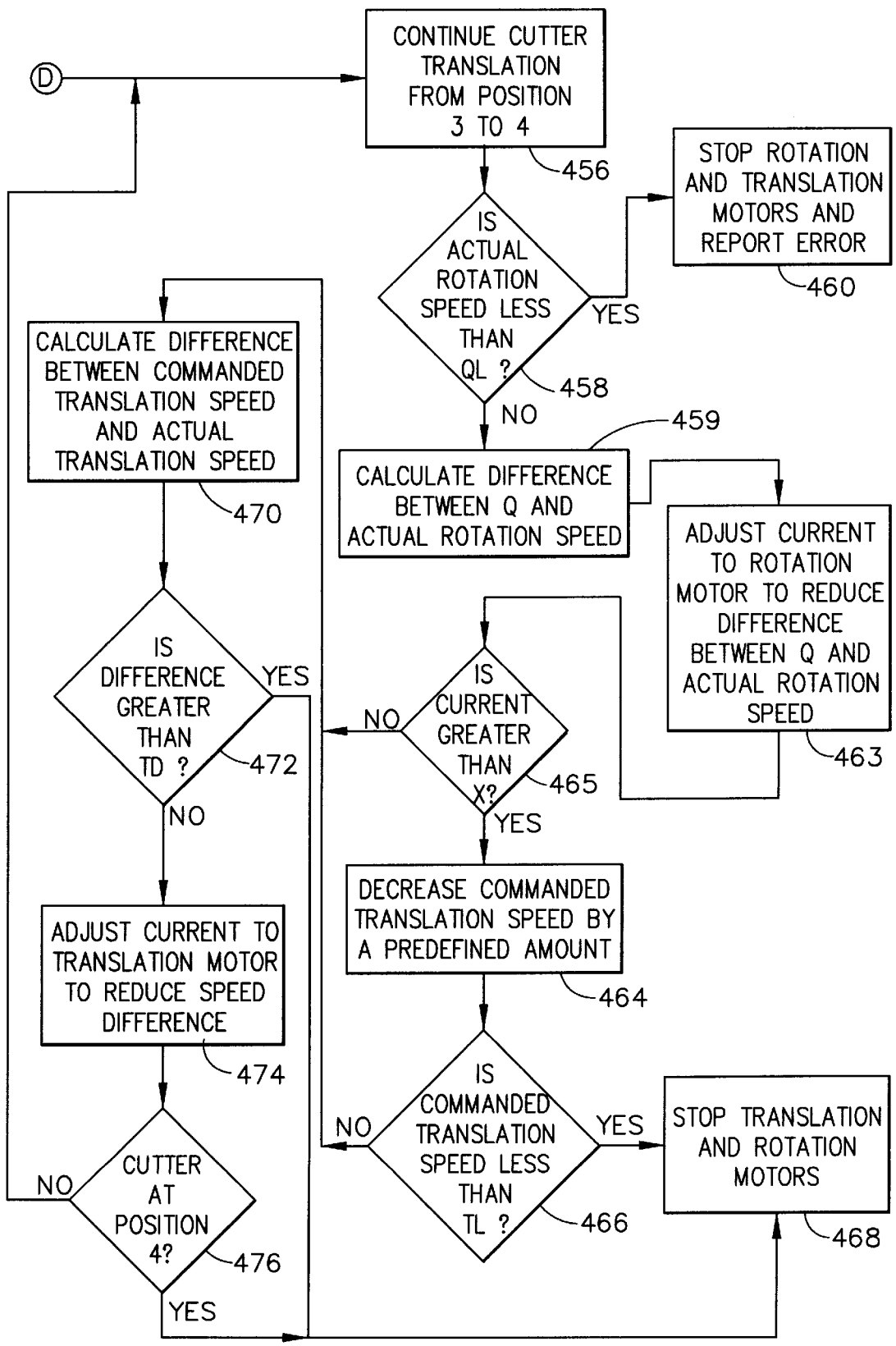
FIG. 17E is a fourth portion of a flow chart pertaining specifically to the second control method embodiment for the operation of the cutter, showing the control unit logic for when the cutter translates from the third position to the fourth position.

Now referring to FIG. 17E which illustrates the last portion of the second control method embodiment, cutter 96 translates from position three to four. In step 456, cutter 96 continues to translate from position three to four. In step 458, actual rotation speed is compared to QL. The difference between the predetermined rotation speed Q and the actual rotation speed is calculated in controller 522 using the signal from the integral encoder of rotation motor 338. If the actual rotation speed is less than QL which is programmed into controller 522, then current to rotation motor 338 and translation motor 340 is stopped. Otherwise, in step 459 the difference is calculated between Q and the actual rotation speed. In step 463, current is adjusted to rotation motor 338 to reduce the difference between Q and the actual rotation speed. Then in step 465, if the current to rotation motor 338 is greater than a value X, the control method proceeds to step 464 where the commanded translation speed is decreased by a predefined amount. The value for X depends on the specifications of the particular motor used. For the example provided in the description of FIG. 14, a preferred value of X is approximately in the range of 3.5 amps. Then the control method continues through the same steps as described for the first control method embodiment of FIG. 17D. If in step 465 the current to rotation motor 338 is not greater than X, then the second control method embodiment proceeds to step 470 and continues through the same steps as described for the first control method of FIG. 17D.

When the operator activates cutter reverse switch 148 (see FIG. 2), cutter 96 translates proximally back to position one at a fourth predetermined translation speed. A value of a fourth predetermined translational speed is approximately in the range of 1.45 inches/second in this embodiment, although this speed may vary for other embodiments. The severed tissue portion is deposited on the tissue sampling surface 64 and may be retrieved by the operator as described earlier. The above control method is repeated for each time a tissue sample is extracted using the "manual" or "sample" modes.

While preferred embodiments of the present invention have been shown and described herein, it will be obvious to those skilled in the art that such embodiments are provided by way of example only. Numerous variations, changes, and substitutions will now occur to those skilled in the art without departing from the spirit and scope of the appended claims.

What is claimed is:

1. A control apparatus for removing at least one tissue sample from a surgical patient using a surgical biopsy device comprising an elongated piercer having a piercer lumen extending therethrough, a cutter rotatably and axially positionable relative to said piercer, said piercer having a port for receiving and transferring said tissue sample into said piercer lumen, said biopsy device further comprising a rotation motor for rotating said cutter and a translation motor for translating said cutter in the axial direction, wherein said control apparatus comprises:
    a) a computing device for the coordinated control of said rotation and translation motors;
    b) a first sensor operationally connected to said rotation motor for supplying a rotation signal to said computing device for measuring the rotational speed of said cutter;
    c) a second sensor operationally connected to said translation motor for supplying a translation signal to said computing device for measuring the translational position and translational speed of said cutter;
    d) a first driver for driving said translation motor in response to a translation command from said computing device; and
    e) a second driver for driving said rotation motor in response to a rotation command from said computing device;
    wherein said control apparatus automatically modifies the rotational speed and the translational speed of said cutter in response to the translational position and rotational resistance acting on said cutter.

2. The control apparatus as set forth in claim 1, wherein said computing device comprises a microprocessor, a non-volatile memory device, and a temporary memory device.

3. The control apparatus as set forth in claim 2, wherein said computing device further comprises a first controller for controlling said translation motor, and a second controller for controlling said rotation motor.

4. A control apparatus for removing at least one tissue sample from a surgical patient using a surgical biopsy device comprising an elongated piercer having a piercer lumen extending therethrough, a cutter rotatably and axially positionable relative to said piercer, said piercer having a port for receiving and transferring said tissue sample into said piercer lumen, said biopsy device further comprising a rotation motor for rotating said cutter and a translation motor for translating said cutter in the axial direction, and wherein said cutter is operationally connected to said translational motor by a flexible, rotatable shaft having a proximal and a distal end, said control apparatus comprising:

a) a computing device for the coordinated control of said rotation and translation motors;

b) a first sensor operationally connected to said rotation motor for supplying a rotation signal to said computing device for measuring the rotational speed of said cutter;

c) a second sensor operationally connected to said translation motor and near the proximal end of said flexible rotatable shaft for supplying a first translation signal to said computing device for determining the translational position and translational speed of said cutter;

d) a first driver for driving said translation motor in response to a translation command from said computing device; and e) a second driver for driving said rotation motor in response to a rotation command from said computing device.

f) a third sensor operationally connected to said translation motor and near the distal end of said first flexible, rotatable shaft for supplying a second translation signal to said computing device, wherein said second translation signal is compared to said first translation signal to determine the translational position of said cutter;

wherein said control apparatus automatically modifies the rotational speed and the translational speed of said cutter in response to the translational position and rotational resistance acting on said cutter.

5. The control apparatus as set forth in claim 4, wherein said computing device comprises a microprocessor, a non-volatile memory device, and a temporary memory device.

6. The control apparatus as set forth in claim 5, wherein said computing device further comprises a first controller for controlling said translation motor, and a second controller for controlling said rotation motor.

7. The control apparatus as set forth in claim 4, wherein said third sensor is an optical encoder.

* * * * *